United States Patent [19]
Fujikura et al.

[11] Patent Number: 5,591,757
[45] Date of Patent: Jan. 7, 1997

[54] DIHYDROPYRIDINE COMPOSITION

[75] Inventors: Takashi Fujikura; Noriki Ito, both of Saitama; Yuzo Matsumoto, Tokyo; Masaharu Asano, Tokyo; Toichi Takenaka, Tokyo, all of Japan

[73] Assignee: Yamanouchi Pharmaceutical Co., Ltd., Tokyo, Japan

[21] Appl. No.: 418,262

[22] Filed: Apr. 6, 1995

Related U.S. Application Data

[63] Continuation of Ser. No. 141,480, Oct. 21, 1993, abandoned, which is a continuation of Ser. No. 865,105, Apr. 8, 1992, abandoned, which is a division of Ser. No. 818,802, Jan. 9, 1992, abandoned, which is a division of Ser. No. 611,340, Nov. 13, 1990, Pat. No. 5,110,820, which is a continuation of Ser. No. 440,441, Nov. 21, 1989, abandoned, which is a continuation of Ser. No. 185,299, Apr. 19, 1988, abandoned, which is a continuation of Ser. No. 913,780, Sep. 30, 1986, abandoned, which is a division of Ser. No. 904,778, Sep. 5, 1986, abandoned, which is a continuation of Ser. No. 692,384, Jan. 17, 1985, abandoned.

[30] Foreign Application Priority Data

Jan. 25, 1984 [JP] Japan ..................... 59-11434

[51] Int. Cl.$^6$ .................................................. A61K 31/455
[52] U.S. Cl. .................................................. 514/356
[58] Field of Search ................................. 514/356

[56] References Cited

U.S. PATENT DOCUMENTS

| | | | |
|---|---|---|---|
| 3,905,970 | 9/1975 | Bossert et al. | 546/321 |
| 4,994,476 | 2/1991 | Poindexter | 546/321 |

*Primary Examiner*—Jane Fan
*Attorney, Agent, or Firm*—Burgess, Ryan and Wayne

[57] ABSTRACT

Pharmaceutical composition of certain dihydropyridine compounds and salts thereof are provided which exhibit both $Ca^{2+}$-antagonistic and adrenergic beta-receptor blocking activities and therefore are useful for the treatment of ischemic heart diseases and hypertension. The pharmaceutical compositions contains either 4-(2-hydroxy-3-phenoxypropylamino)-butyl methyl 2,6-dimethyl-4-(m-nitrophenyl)-1,4-dihydropyridine-3,5-dicarboxylate or 6-(2-hydroxy-3-phenoxypropylamino) hexyl methyl 2,6-dimethyl-4-(m-nitrophenyl)-1,4-dihydropyridine-3,5-dicarboxylate or their pharmaceutically acceptable salts.

1 Claim, No Drawings

DIHYDROPYRIDINE COMPOSITION

This application is a continuation of application Ser. No. 08/141,480, filed Oct. 21, 1993 now abandoned which is a continuation of application Ser. No. 865,105, filed Apr. 8, 1992, now abandoned which is a divisional of application Ser. No. 07/818,802, filed Jan. 9, 1992, now abandoned, which in turn is a divisional of Ser. No. 07/611,340, now abandoned, filed Nov. 13, 1990, now U.S. Pat. No. 5,110,820, which is a continuation of application Ser. No. 07/440,441, filed Nov. 21, 1989, now abandoned, which, in turn, is a continuation of Ser. No. 07/185,299, filed Apr. 19, 1988, now abandoned, which is a continuation of Ser. No. 06/913,780, filed Sep. 30, 1986, now abandoned, which, in turn, is a divisional application of Ser. No. 06/904,778, filed Sep. 5, 1986, now abandoned, which is a continuation of Ser. No. 06/692,384, filed Jan. 17, 1985, now abandoned.

BACKGROUND OF THE INVENTION

It is known that certain dihydropyridine derivatives have a $Ca^{2+}$-antagonistic action, and are highly useful for treatment of various cardiovascular disorders such as angina pectoris, myocardial infarction, hypertension and cardiac arrythmia. It is further known that beta-adrenoceptor blocking agents are also useful for the treatment of such cardiovascular disorders.

However, the mechanism of actions of dihydropyridine derivatives is entirely different from that of beta-adrenocaptor blocking agents. That is, beta-adrenoceptor blocking agents reduce heart rate, cardiac output, stroke volume, cardiac work and myocardial oxygen demand whereas, $Ca^{2+}$-antagonists improve left ventricular function due to their coronary vasodilating and systemic vasodilating effect (reduction in afterload) and also inhibit coronary vasospasm.

Recently it has been reported that a combined administration of a $Ca^{2+}$-antagonist and a beta-blocker can achieve maximal symptomatic improvement in clinical angina pectoris. [Bassan, M., Wiler-Ravell, D. and Shalev, O.; Additive antianginal effect of verapamil in patients receiving propranolol; Br. Med. J., 284, 1067 (1982)]. Further it has been reported that a combined administration of such two kinds of drug can be recommended for the treatment of hypertension, since the side effects of either drug are almost abolished or inhibited by the combination administration of both drugs. That is, beta-blocker inhibits a $Ca^{2+}$-antagonist-induced reflex increase of heart rate; and beta-blocker completely inhibit a $Ca^{2+}$-antagonist-induced increase of plasma renin activity. [Aoki, A., Kondo, S., Mochizuki, A., et al; Antihypertensive effect of Cardiovascular $Ca^{2+}$-antagonist in hypertensive patients in the absence and presence of beta-adrenergic blockade; Am. Heart J., 96, 218 (1978)]

Thus, it would be expected that a compound having both $Ca^{2+}$-antagonistic and beta-blocking activities are of interest in the management of ischemic heart-diseases and hypertension.

However, any compound having such both actions is not known until now. That is, it has never been reported that a compound having both $Ca^{2+}$-antagonistic and beta-blocking activities has been synthesized. Thus the purpose of this invention is to provide novel compounds which have both the actions (namely, $Ca^{2+}$-antagonistic activity and adrenergic beta-receptor blocking activity) and the production methods for the compounds.

DETAILED EXPLANATION OF THE INVENTION

This invention relates to novel 1,4-dihydropyridine derivatives, the production of these compounds, medical compositions containing them, and salts thereof.

The compounds of this invention are those of the general formula (I) and salts thereof:

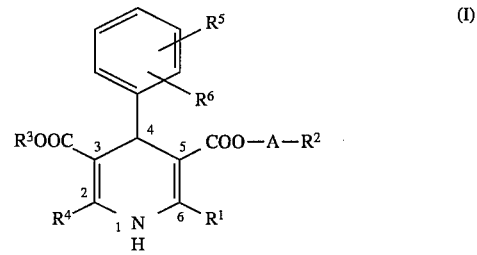

wherein A represents a straight or branched carbon chain alkylene group having 1 to 10 carbon atoms which may be interrupted by an oxygen atom(s); $R^1$ and $R^4$, which may be the same or different, each represents a lower alkyl group; $R^2$ represents an amino group,

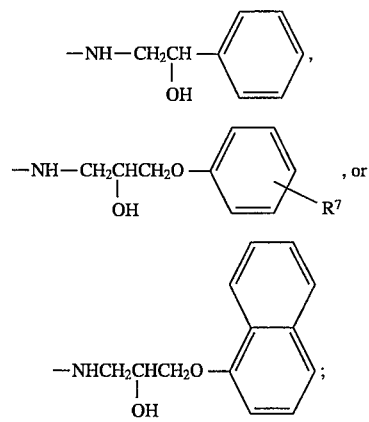

$R^3$ represents a straight or branched carbon chain alkyl group having 1 to 10 carbon atoms which may be interrupted by an oxygen atom(s), or

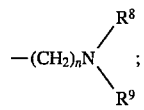

$R^5$ and $R^6$, which may be the same or different, each represents a hydrogen atom, a nitro group, a halogen atom, a trifluoromethyl group, a cyano group, a lower alkyl group, a lower alkoxy group or a lower alkenyloxy group; $R^7$ represents a hydrogen atom, a cyano group, a halogen atom, a lower alkoxy group or a lower alkanoyl group; $R^8$ and $R^9$, which may be the same or different, each represents a lower alkyl group or an aralkyl group; and n represents an integer of 1 to 2; these symbols, hereafter, have the same significances.

The compounds of this invention posses both $Ca^{2+}$-antagonistic and adrenergic beta-receptor blocking activities.

The term "lower alkyl" in the foregoing definitions for $R^1$, $R^4$, $R^5$, $R^6$, $R^8$ and $R^9$ means a straight or branched carbon chain alkyl having 1 to 4 carbon atoms. Thus examples of the "lower alkyl" are methyl, ethyl, n-propyl, iso-propyl, n-butyl, iso-butyl, sec-butyl, and tert-butyl.

The term "lower alkoxy" in the foregoing definitions for $R^5$, $R^6$ and $R^7$ means an alkoxy having 1 to 4 carbon atoms. Thus examples of the "lower alkoxy" are methoxy, ethoxy, propoxy, iso-propoxy, n-butyoxy, sec-butoxy, and tert-butoxy.

The term "lower alkenyloxy" in the foregoing definitions for $R^5$ and $R^6$ means an alkenyloxy having 1 to 4 carbon atoms. Thus examples of the "lower alkenyloxy" are vinyloxy, 1-propenyloxy, allyloxy, 1-butenyloxy, 2-butenyloxy, and 3-butenyloxy. As the examples of "lower alkanoyl" in the definition for $R^7$ there are acetyl, propionyl, butyryl (butanoyl), etc.

As the examples of the "halogen" in the definition for $R^5$, $R^6$ and $R^7$, there are chlorine, bromine, iodine, etc. As the examples of "aralkyl" in the definitions for $R^8$ and $R^9$, there are benzyl, phenethyl, phenylpropyl, etc.

As the examples of "straight or branched carbon chain alkyl having 1 to 10 carbon atoms which may be interrupted by oxygen atom" in the definition for $R^3$, there are methyl, ethyl, propyl, iso-propyl, butyl, iso-butyl, sec-butyl, tert-butyl, pentyl(amyl), iso-pentyl, tert-pentyl, neo-pentyl, hexyl, iso-hexyl, 1-methylpentyl, 2-methylpentyl, 3-methylpentyl, 1,1-dimethyl-butyl, 1,2-dimethylbutyl, 1,3-dimethylbutyl, 2,2-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, 1-methylhexyl, 2-ethylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 1-ethylpentyl, 2-ethylpentyl, 3-ethylpentyl, 1,1,2-trimethylbutyl, 1,1,3-trimethylbutyl, 1,2,2-trimethylbutyl, 2,2,3-trimethylbutyl, 1-ethyl-1-methylbutyl, 1-ethyl-2-methylbutyl, 1-ethyl-3-methylbutyl, 1-propylbutyl, 1-isopropylbutyl, octyl, 6-methylheptyl, nonyl, 7-methyloctyl, decyl, 8-methylnonyl, etc.; in addition, there are methoxymethyl, 1-methoxhethyl, 2-methoxyethyl, 1-methoxypropyl, 2-methoxypropyl, 3-methoxypropyl, 1-methoxy-1-methylethyl, 2-methoxy-1-methylethyl, 1-methoxybutyl, 2-methoxybutyl, 3-methoxybutyl, 4-methoxybutyl, 3-methoxy-1-methylpropyl, ethoxymethyl, 1-ethoxyethyl, 2-ethoxyethyl, 1-ethoxypropyl, 2-ethoxypropyl, 3-ethoxypropyl, propoxymethyl, iso-propoxymethyl, 1-propoxyethyl, 1-isopropoxyethyl, 2-propoxyethyl, 2-iso-propoxyethyl, 6-methoxyheptyl, 7-methoxyoxtyl, 8-methoxynonyl, etc., as the example of such alkyl interrupted by oxygen atom.

As the examples of "straight or branched carbon chain alkylene having 1 to 10 carbon atoms which may be interrupted by oxygen atom" in the definition for A, there are straight or branched carbon chain divalent alkylene having 1 to 10 carbon atoms and straight or branched carbon chain divalent alkylene having 2 to 10 carbon atoms which may be interrupted by oxygen atom (that is, ether type alkylene). As the practical examples for these groups, there are methylene, methylmethylene

ethylene, trimethylene, propylene

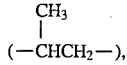

tetramethylene, 1-methyltimethylene

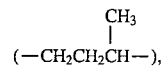

2-methyltrimethylene, 3-methyltrimethylene, 1-ethylethylene

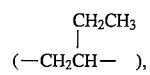

2-ethylethylene, pentamethylene, hexamethylene, heptamethylene, oxtamethylene, nonamethylene, decamethylene, 2-oxabutan-1,4-diyl ($-CH_2-OCH_2CH_2-$), 3-oxapentan-1,5-diyl ($-CH_2CH_2OCH_2CH_2-$), 2-oxypentan-1,5-diyl ($-CH_2OCH_2CH_2CH_2$), 3-methyl-2-oxapentan-1,5-diyl

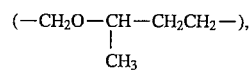

5-methyl-2-oxahexan-1,6-diyl

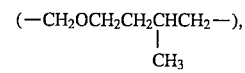

etc.

The salts of the compound (I) include pharmaceutically acceptable nointoxic salts or pharmacologically acceptable salts. Examples of such salts are, for example, salts of inorganic acids such as hydrochloric acid, hydrobromic acid, hydroiodic acid, sulfuric acid, nitric acid, phosphoric acid, hydroiodic acid, sulfuric acid, nitric acid, phosphoric acid; and salts of organic acids such as formic acid, acetic acid, oxalic acid, ctric acid, succinic acid, fumaric acid, maleic acid, tartaric acid, methanesulfonic acid, ethanesulfonic acid, etc.

The compounds of this invention include compounds having asymmetric carbon atoms(s); and in case of such compounds, there are optical isomers. Thus this invention includes all of the isomers such as racemic compound, optically active isomer, diastereoisomer, etc.

The compounds of this invention can be produced by various processes; typical production processes are explained hereinafter:

Process 1:

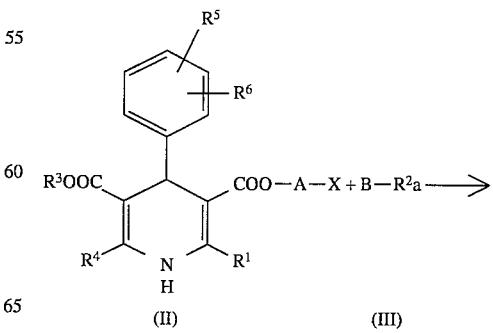

-continued

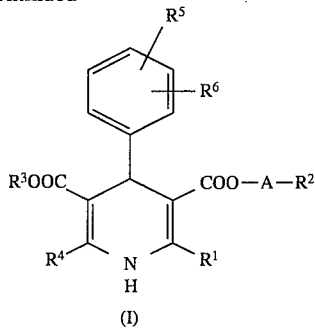

In the above formulas, A, $R^1$, $R^2$, $R^3$, $R^4$, $R^5$, $R^6$, $R^7$, $R^8$, $R^9$, and n are as defined above; X represents a halogen atom, $R^2$a represents a hydrogen atom,

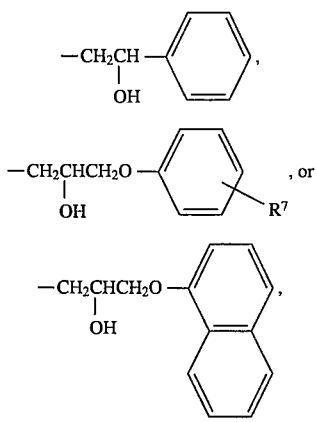

wherein $R^7$ is as defined above, B represents an amino group or a protected amino group; and $R^2_a$ represent a potassium atom when B represents a phthalimid group

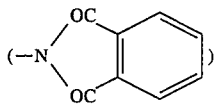

as protected amino.

Compounds (I) can thus be produced by reacting dihydropyridine derivative (II) [which have halogenoalkyl (or halogenoalkoxyalkyl) ester group as the substituent at 5-position of the dihydropyridine ring] with amine compound or amine derivative (III) and the, if necessary (that is, when B is a protective amino group), releasing the protective group.

Practical examples of "halogen" for X are chlorine, bromine, iodine; and practical examples of the protective group for an amino group are a toluenesulfonyl group, an acetyl group, a phenacylsulfonyl group, a trifluoromethanesulfonyl group, a bis-benzenesulfonyl group; further, potassium phthalimide is included in the compound $R^2$a-B having a protected amino group. That is, Gabriel amine synthesis via phthalimide compound using potassium phthalimide can be applied for producing the compound (I).

One of the above reactions is alkylation with compound (II). In case of reacting ammonia as the compound (III) to produce an primary amine as the compound (I), there may be occur some side-reactions such as, particularly, polyalkylamine formation or amidation reaction; in such case, it is preferred to adopt the amino-protected compound (III) in order to produce the desired compound (I) selectively. In case of reacting this compound (III) other than ammonia, it is not always necessary to adopt the amino-protected compound (III). By adopting suitable reaction conditions, amino-protection is not needed.

The reaction can be performed in the presence or absence of a solvent. It is preferred to perform the reaction in a solvent. Any solvents which do not take part in the reaction can be used. Examples of the solvent usually used are organic solvent such as benzene, toluene, xylene, dimethylformamide, dichloromethane, dichloroethan, methanol, ethanol. In case of adopting phthalimide compound as the compound (III) [that is, in case of Gabriel method], dimethylformamide or xylene is usually used; particularly, in case of using dimethylformamide, the reaction can performed under considerably mild reaction conditions. The above solvents may be used along or in appropriate combination.

It is preferred that the reaction is performed by reacting the compound (II) with an equimolar or excessive molar amount of the compound (III).

According to the kind of reaction, it may be preferred for smooth reaction to operate in the presence of a base. Examples of such a base are organic bases such as pyridine, picoline, N,N-dimethylaniline, N-methylmorpholine, dimethylamine (that is, secondary or tertiary amines); and inorganic bases such as sodium carbonate, potassium hydrogencarbonate. It may be preferred for smooth reaction to operate by using the increased amount of the compound (III). Thus, various operation conditions may be adopted.

The reaction is usually performed at room temperature or under heating, or under reflux at heating.

When using protected amine compound as the compound (III), after hydrolysis reaction in conventional manner, the aimed compound (I) can be produced. The hydrolysis is performed by acid- or alkali-hydrolysis, and Ing-Manske hydrolysis using hydrazine. Among them, Ing-Manske hydrolysis is preferred. (That is, hydrazine hydrolysis is more advantageous than acid- or alkali-hydrolysis.)

Starting materials (that is, the compounds (II)) can be easily available since the compounds can be easily prepared by the methods described in U.S. Pat. No. 3,985,758 (applicants: some of the inventors of this application). That is, the starting materials can be synthesized by Hantzsch synthesis method or the modified method thereof.

Process 2:

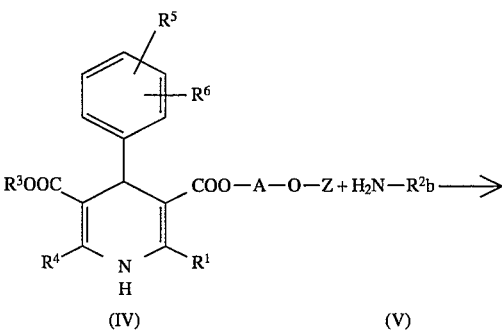

-continued

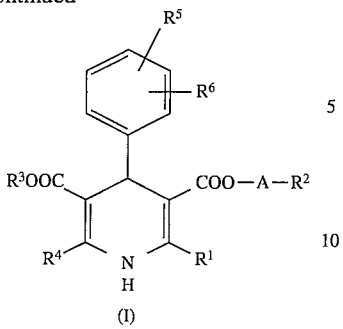

wherein Z represents a organic sulfonic acid radical; $R_2b$ represents a hydrogen atom,

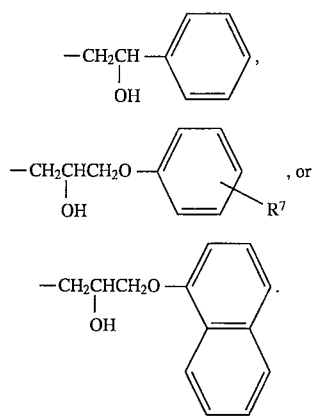

Compounds (I) can thus be prepared by reacting organic sulfonate compound (IV) with amine compound (V).

In this case, examples of organic sulfonic acid radical are alkanesulfonic acid radical (alkylsulfonyl group) such as methanesulfonic acid radical (metahensulfonyl), ethanesulfonic acid radical (ethanesulfonyl); and aromatic sulfonic acid radical such as toluenesulfonyl acid radical (toluenesulfonyl), benzenesulfonic acid radical (benzenesulfonyl), etc. An equimolar or excess molar amount of the compound (V) is preferably reacted with the compound (IV). The reaction is usually performed at room temperature or under cooling. The reaction is usually performed in a solvent which do not take part in the reaction, and the examples of the solvent are ether, methanol, ethanol, toulene, tetrahydrofuran. The reaction time may be changed according to the kind of starting material & solvent, and the reaction conditions such as the reaction temperature.

Process 3:

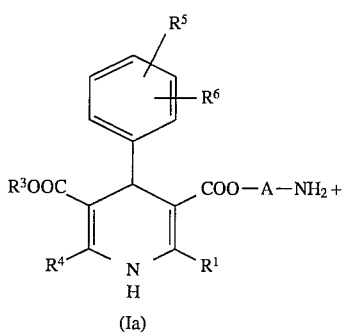

-continued

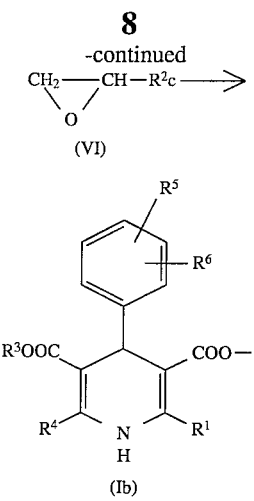

wherein $R^2c$ represents a phenyl group, a phenoxymethyl group which may be substituted by a $R^7$ group, or a naphthyloxymethyl group; $R^7$ is s defined above.

The above compounds ($I_b$) [that is, the compounds (I) wherein $R^2$ is the above-defined group other than an amino group] can be produced by reacting the compound ($I_a$) [that is, the compound (I) wherein $R^2$ is an amino group] with the above epoxy compound (VI).

An equimolar or excess molar amount of either of the compounds ($I_a$) and (VI) is used for the reaction, and the reaction is performed in the absence or presence of a solvent which do not take part in the reaction. The examples of the solvent are organic solvent such as alcohol, (e.g. methanol, ethanol), ether (e.g. ethyl ether), tetrahydrofuran, ethyl acetate, etc. The reaction can be performed at room temperature or under heating. The reaction time may be changed according to other reaction conditions such as the solvent, etc.

Process 4:

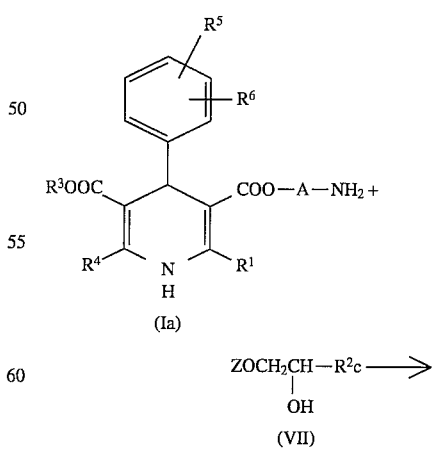

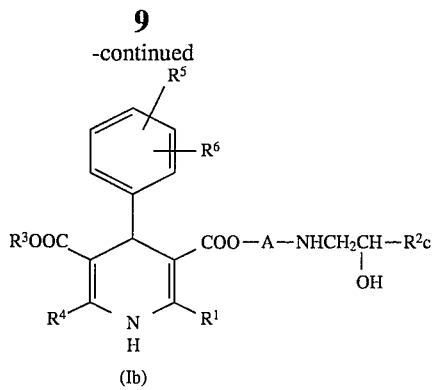

(Ib)

wherein Z represents an organic sulfonic acid radical as defined above. $R^1$, $R^2c$, $R^3$, $R^4$, $R^5$, $R^6$ are as defined above.

The compounds ($I_b$) can also be prepared by reacting the compound ($I_a$) with the organic sulfonic acid derivative (VII).

An equimolar or excess molar amount of either of the compounds ($I_a$) and (VII) is used for the reaction, and the same solvent and the same reaction conditions as in the Process 2 is adopted in the reaction.

Starting materials ($I_a$) in the above Process 3 and 4 may be produced by the method described in U.S. Pat. No. 3,985,758 using Hantzsch synthesis method. However, these starting materials ($I_a$) can be preferably produced by the method described in the Reference Examples of this application. This method described in the Reference Examples is based on a novel reaction for dihydropyridine ring formation which, per se, is not known until now. And the new method has various advantages over known methods such as that of the U.S. Patent. That is, in the case of the novel method for dihydropyridine ring, there scarcely occur side-reaction, and 5-aminoalkoxycarbonyl compounds ($I_a$) can be produced selectively in high yield.

A free form of the formula (I) compound or a salt of the compound (I) can be obtained after the above reactions. A salt of the formula (I) compound may be produced by performing the foregoing production process using a salt of the starting compound, or by applying a salt-forming reaction to the free formula (I) compound.

The formula (I) compounds and salts can be separated and purified in ordinary manner, such as extraction with organic solvent, crystallization, column chromatography.

The compounds of this invention of the formula (I) or salts thereof possess $Ca^{2+}$-antagonistic activity and adrenergic beta-receptor blocking activity, and further possess intrinsic sympathomimetic activity (ISA). Thus the compounds have scarcely side effects, and the compounds are useful for treatment or prevention of ischemic heart-diseases such as angina pectoris, myocardial infarction, and also useful for treatment or prevention of cardiovascular disorders such as hypertension, cardiac arrythmia.

The compounds of this invention possess also cerebral vasoconstriction-depressing action and central nervous system-improving action in addition to cardiovascular actions. So the compounds may be also a agent useful for depressing cerebral vasoconstriction and improving central nervous system.

Effective dose of the compounds of this invention is from 0.001 to 3 mg/kg (intravenous injection) in the case of antihypertensive effect and coronary blood flow increasing effect; is from 1 to 300 µg/kg (intracoronary injection) in the case of coronary vasodilating effect; and is from 0.1 to 3 mg/kg (intravenous injection) in the case of beta-blocking activity. In these cases, it was also found that the compounds of this invention reduce cardiac work and myocardial oxygen demand.

Moreover, it was found that antihypertensive activity and coronary vasodilating activity of the compounds of this invention are effective for a more long period of time than in the case of known dihydropyridine compounds.

The pharmacological effects of the compounds of this invention are shown in the following test results with the test methods.

Methods (1) Hemodynamic effects

Mongrel dogs of either sex were anesthetized with pentobarbital sodium (30 mg/kg iv). The animals were artificially ventilated with room air. The chest was opened at the left 4th intercostal space. Mean arterial blood pressure (MBP), heart rate (HR), left ventricular pressure (LVP), max. dLVP/dt, mean pulmonary arterial blood pressure (MPAP), cardiac output (CO) and coronary blood flow (Cor. BF) were measured. The test compounds were injected into the femoral vein. Hemodynamic effects of these compounds were compared with that of well known $Ca^{2+}$-antagonists.

Table 1 (column 1) indicates the percent changes of MBP and Cor. BF from control values induced by intravenous injection of test compounds.

(2) Coronary vasodilating effects

Mongrel dogs of either sex were anesthetized and ventilated as previously described. A thoracotomy was performed at the 4th intercostal space. Following an intravenous injection of heprin (1000 units/kg), blood from the distal end of the cannulated carotid artery was pumped into circumflex branch of the left coronary artery using a servocontrolled peristaltic pump which maintained a constant perfusion pressure of 120 mmHg by means of a pump controller. An electromagnetic flow probe was inserted in the circit to record blood flow through the cannulated coronary artery. The test compounds were administered directly into the rubber tubing connected close to the coronary artery cannula. Coronary vasodilating potency of the test compounds was by calculating the does required to produce 100% increase of Cor. BF ($ED_{100}$ pap), when the maximum responses to papaverine at a dose of 300 µg ia was expressed as 100% response. Table 1 (column 2) shows $ED_{100}$ pap and the duration of action of coronary vasodilating effect of test compounds.

(3) Beta-adrenoceptor blocking effects

Beta-adrenoceptor blocking effect of test compounds was determined according to the method of Tachikawa and Takenaka (Pharmocological studies on 1-(7-indenyloxy)-3-isopropylaminopropan-2-ol hydrochloride (YB-2); Arch. Int. pharmacodyn., 202, 79–92, 1973) using male Wistar rats. The rats were pretreated with reserpine (8 mg/kg ip), 18 hr before experiments. The rats were anesthetized with pentobarbital sodium (55 mg/kg ip) and vagotomized bilaterally at the neck. The heart rate was measured with a cardiotachometer triggered by the QRS of the ECG (lead II) and recorded on a polygraph. After the Control response to isoproterenol at a dose of 0.1 µg/kg iv was obtained, the test compound was injected iv in increasing doses at 20 min intervals. The mean dose producing 50% blockade of the positive chronotropic response to isoproterenol ($ED_{50}$) was estimated from dose-response curves obtained by plotting inhibition percentage against log cumulative dose of the test compound (Table 1, column 3).

In this series of experiments, intrinsic sympathomimetic activity (ISA) was also evaluated. The results were shown in Table 1 (column 4), wherein "−" represents that an increase in HR was scarcely observed; "+" represents that an increase in HR by 10 to 19 beats/min was observed; "++" represents that an increase in HR by 20 to 29 beats/min was observed; "+++" represents that an increase in HR by above 30 beats/min.

Jap. J. Pharmacol., 34, Suppl. Abst. No. 0–151, 1984) using circular segments of dog coronary artery. The ring segments were cannulated with two triangle stainless-steel hooks and suspended vertically in Krebs-Henseleit solution under the same condition described previously. Preparations were set up under a resting tension of 1.0 g and rhythmic contractions were induced by application of 10 mM 3,4-DAP. Test compound was cumulatively added into the medium. $IC_{50}$

TABLE 1

Summary of pharmacological effects of test compounds

| Ex. No. | (1) MBP mg/kg iv | (%) | Cor. BF (%) | (2) $ED_{100}$ pap μg ia | Duration min | (3) Beta-Blocking $ED_{50}$ mg/kg iv | (4) ISA |
|---|---|---|---|---|---|---|---|
| 7 | 1.0 | −20 | 24 | 100 | 60< | 1.93 | − |
| 11 | 0.1 | −16 | 35 | 150 | 60 | 0.64 | ++ |
|  | 1.0 | −41 | 193 |  |  |  |  |
| 12 | 0.3 | −26 | 45 | 100 | 60< | 0.60 | − |
| 13 | 0.03 | −21 | 102 | 12 | 60 | 0.72 | + |
| 18 | 0.3 | −22 | 31 | 67 | 60< | 1.25 | − |
| 21 | 1.0 | −28 | 34 | 137 | 60 | 1.01 | + |
| 22 | 0.3 | −22 | 118 | 128 | 60 | 0.82 | − |
| 30 | 0.1 | −21 | 12 |  |  | 0.79 | − |
| 32 | 0.1 | −18 | 35 |  |  | 1.18 | − |
|  | 0.3 | −36 | 93 |  |  |  |  |
| 41 | 0.3 | −34 | 45 | 43 | 60< | 0.58 | +++ |
| 43 | 0.3 | −22 | 44 | 56 | 60< | 0.87 | − |
| 46 | 0.3 | −21 | 36 | 98 | 60< | 0.66 | + |
|  | 1.0 | −45 | 78 |  |  |  |  |
| 47 | 0.3 | −34 | 30 | 245 | 60< | 0.11 | +++ |
|  | 1.0 | −44 | 57 |  |  |  |  |
| 48 | 0.3 | −20 | 71 | 76 | 60 | 0.68 | − |
|  | 1.0 | −43 | 92 |  |  |  |  |
| Verapamil | 0.1 | −23 | 95 | 8 |  | NE |  |
| Propranolol |  | NT |  | NT |  | 0.063 | − |

NE = No effect, NT = Not tested

Ca-Antagonistic and beta-adrenoceptor blocking effect of the compound of this invention (in the case of the compound of Example 12, namely, 6-(2-hydroxy-3-phenoxypropylamino)hexyl methyl 2,6-dimethyl-4-(m-nitrophenyl)-1,4-dihydropyridine-3,5-dicarboxylate) were investigated by using the following in vitro experiments.

$Ca^{2+}$-Antagonism (1) Effect on KCl-induced contraction

The experiment was performed according to the method of Terai, Takenaka and Maeno (Inhibition of calcium influx in rabbit aorta by nicardipine hydrochloride (YC-93); Bioch. Pharmacol., 30, 375–378, 1981). Herical strips were prepared from a rabbit thoracic aorta. The strips were incubated in 30 ml Krebs-Henseleit solution which was maintained at 37 C. and was constantly aerated with 95% $O_2$ and 5% $CO_2$ gas mixture. Isometric contractions were measured under a resting tension of 2.0 g. The strips were contracted by the addition of 50 mM KCl. Test compound was cumulatively added into the medium. The mean concentration producing a 50% inhibition of the KCl-induced contraction ($IC_{50}$) was estimated from dose-response curves (Table 2, column 1).

(2) Effect on 3,4-diaminopyridine (3,4-DAP)-induced rythmic contraction

The experiment was performed according to the method of Uchida and Sugimoyo (Mechanism of rythmic contraction of coronary artery and the effect of nicorandil (SG-75);

was estimated from dose-response curves (Table 2, column 2).

(3) Effect on [$^3$H]-nitrendipine binding

The inhibitory effect of test compound on [$^3$H]-nitrendipine binding to rat brain membrane was evaluated according to the method of Gould, Murphy and Synder ([$^3$H]-Nitrendipine-labeled calcium channels discriminate inorganic calcium agonosts and antagonists; Proc. Nati. Acad. Sci. USA, 79, 3656–3660, 1982). The $IC_{50}$ values, the concentration required to inhibit specific binding by 50%, were computed by logit-log analysis and then the inhibition constant (Ki) was obtained (Table 2, column 3).

Beta-adrenoceptor blocking effect

According to the method of Takenaka, Shiono, Honda, Asano, Miyazaki and Maeno (Antihypertensive and adrenoceptor blocking properties of new sulfonamide-substituted phenylethylamines; Clin. and Exper. Hyper.- Theory and Practice, A4, 125–137, 1982), isolated rate right atria was mounted in organ baths containing 30 ml of Krebs-Hensaleit solution under same condition described previously. Beta-adrenoceptor blocking effect of test compounds was estimated by antagonism of (−)-isoproterenol-induced positive chronotropy. Antagonist dissociation constants ($K_B$) were determined at each concentration of test compound from dose-response cureves and then $pA_2$ was calculated as −log $K_B$ (Table 3).

TABLE 2

| | Ca$^{2+}$-antagonism of Ex. 12, nicardipine, verapamil and propranolol | | | | |
|---|---|---|---|---|---|
| | Rabbit aorta K contraction | Dog coronary artery 3,4-DAP contraction | $^3$H-Nitrendipine binding | | |
| Compound | IC$_{50}$ (×10$^{-9}$M) | IC$_{50}$ (×10$^{-9}$M) | IC$_{50}$ (×10$^{-9}$M) | Ki | Slope |
| Ex. 12 | 33 | 19 | 12 | 6.15 | 1.38 |
| Nicardipine | 1 | 2.1 | 1.6 | 0.9 | 0.90 |
| Verapamil | 75 | 126 | —* | — | — |
| Propranolol | NE | NE | | NE | |

*Verapamil (> 100 μM) did not produce 50% displacement of $^3$H-nitrendipine binding.
NE = No effect

TABLE 3

| Beta-adrenoceptor blocking activity of Ex. 12, nicardipine, verapamil and propranolol | | |
|---|---|---|
| | Beta-blocking activity Isolated rat rught atria | |
| Compound | K$_B$ (×10$^{-9}$M) | pA$_2$ |
| Ex. 12 | 63 | 7.20 |
| Nicardipine | NE | |
| Verapamil | NE | |
| Propranolol | 2.1 | 8.67 |

NE = No effect

Medicaments containing compounds according to the invention may be prepared by conventional methods using conventional carriers or excipients. Medicants may contain one kind of the compound or many kinds of the compound of this invention. The compound may be free form compound or salt thereof. They may for example be administered orally as tablets, pills, capsules, granules; parenterally by intravenous or intramuscular injection; or suppositories.

The appropriate dose is determined in each case considering factors such as the symptom, age and sex of the patients. For an adult a daily total of 1–200 mg is usually administered by intravenous injection in one to several doses.

Then, the manufacturing process and the process of this invention will further explained by the following Reference Examples and the following Examples, respectively.

REFERENCE EXAMPLE

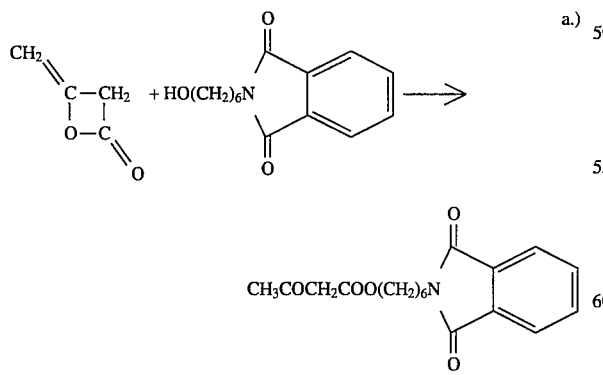

In 290 ml of tetrahydrofuran were dissolved 48.3 g of 6-phthalimido-1-hexanol and 1.2 ml of triethylamine, and 18.1 g of diketene was added dropwise thereto under reflux over a period of 30 minutes. After refluxing the mixture for 1.5 hours; the mixture was cooled to room temperature, and then concentrated under reduced pressure. The residue was extracted with chloroform, and the extract was washed with dilute aqueous hydrochloric acid and water, dried over anhydrous magnesium sulfate, and concentrated under reduced pressure to provide 61.2 g of a crude product of 6-phthalimidohexylacetoacetate. Thie crude product was used for the next reaction step, without purification.

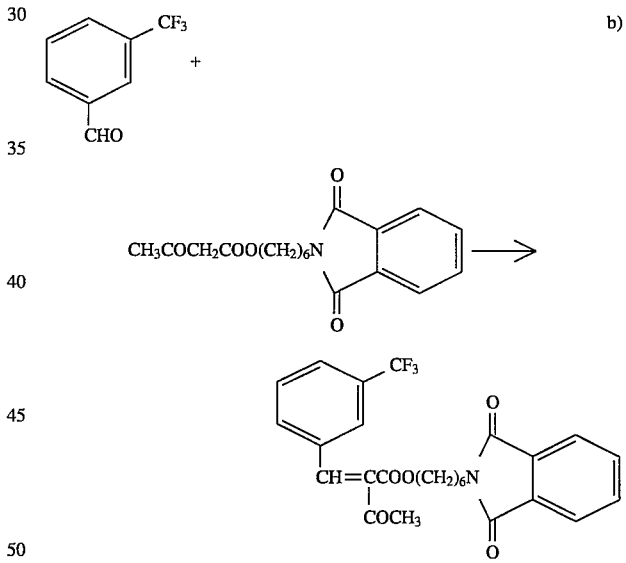

In 72 ml of dry benzene were dissolved 13.0 g of 6-phthalimidohexylacetoacetate, 6.85 g of m-trifluoromethylbenzaldehyde, 0.17 ml of piperidine and 0.51 ml of acetic acid. The mixture was refluxed under heating for 4.5 hours while removing formed water by using Dean-Stark trap. The reaction solution was cooled, and concentrated under reduced pressure. The residue was subjected to silica gel column chromatography, and the product was eluted with chloroform. 11.24 g of a crude product of 6-phthalimidohexyl 2-(m-trifluoromethylbenzilidene)acetoacetate was obtained. This product was used for the following reaction, without purification

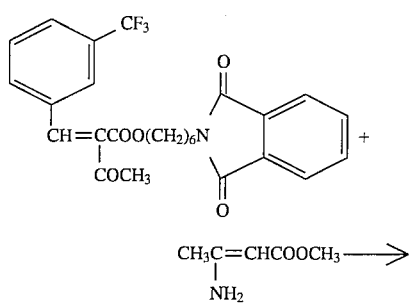

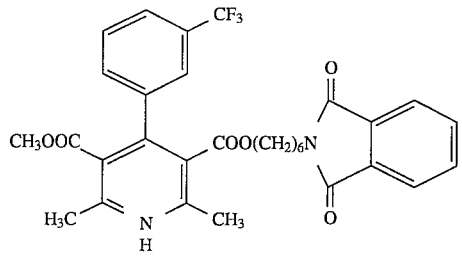

In 92 ml of isopropylalcohol were dissolved 10.2 g of 6-phthalimidohexyl 2-(m-trifluoromethylbenzilidene)acetoacetate and 2.4 g of methyl 3-aminocrotonate, and the mixture was refluxed under heating for 3.5 hours. After cooling the reaction solution to room temperature, the solution was concentrated under reduced pressure to provide 12.5 g of a crude product of methyl 6-phthalimidohexyl 2,6-dimethyl-4-(m-trifluoromethylphenyl)-1,4-dihydropyridine-3,5-dicarboxylate. This product was used for the following reaction, without purification.

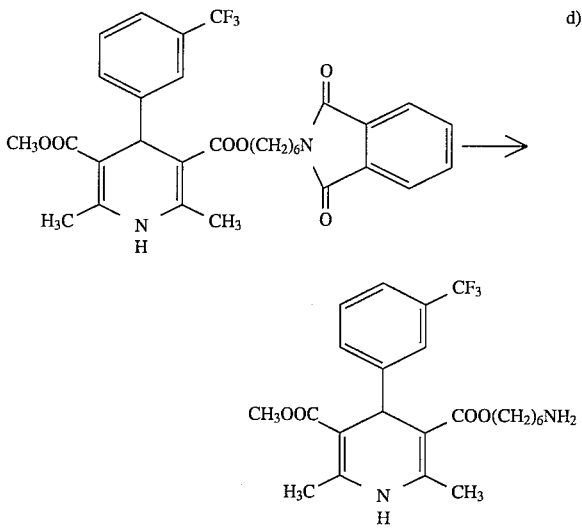

A solution of 11.2 g of methyl 6-phthalimidohexyl 2,6-dimethyl-4-(m-trifluoromethylphenyl)-1,4-dihydropyridine-3,5-dicarboxylate and 10.1 g of hydrazine monohydrate in 330 ml of 95% ethanol (containing water of 5%) was refluxed for 4 hours under heating. After cooling the reaction solution, the solution was concentrated under reduced pressure. The residue was extracted with chloroform, and the extract was washed with water, dried over anhydrous magnesium sulfate, and concentrated. Crude crystal were recrystallized from chloroform-ether to provide 2.6 g of 6-aminohexyl methyl 2,6-dimethyl-4-(m-trifluoromethylphenyl)-1,4-dihydropyridine-3,5-dicarboxylate.

Melting point: 119°–120.5° C.

Elemental analysis for $C_{23}H_{29}O_4N_2F_3 \cdot 0.2\ H_2O$

|  | C(%) | H(%) | N(%) | F(%) |
|---|---|---|---|---|
| Calculated: | 60.31 | 6.47 | 6.12 | 12.44 |
| Found: | 60.39 | 6.36 | 6.27 | 12.26 |

NMR (CDCl$_3$) δ: 2,33 (6H,s), 2.66 (2H,t), 3.65 (3H,s), 3.93–4.13 (2H,m), 5.05 (1H, s), 6.10 (1H, s)

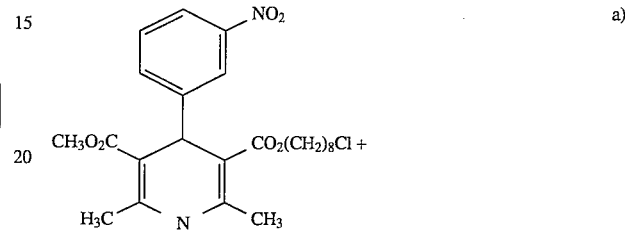

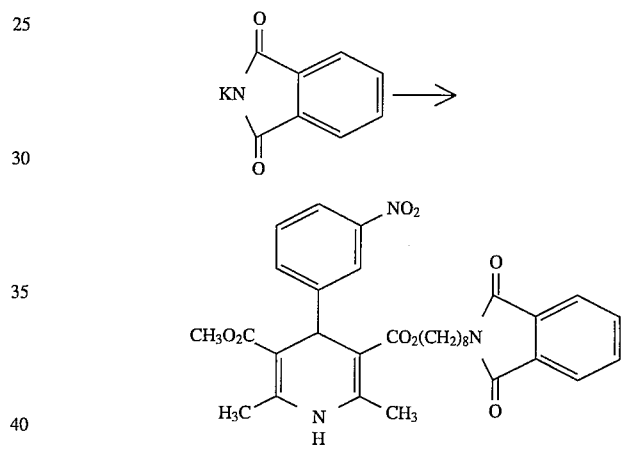

In 20 ml of N,N-dimethylformamide were dissolved 14.3 g of 8-chlorooctyl methyl 2,6-dimethyl-4-(m-nitrophenyl)-1,4-dihydropyridine-3,5-dicarboxylate and 6 g of potassium phthalimide, and the mixture was refluxed for 3 hours under heating at 140°–150° C.

The reaction mixture was cooled to room temperature and after adding water thereto, the mixture was extracted with ether. The extract was washed with water, dried, and concentrated under reduced pressure to provide 16.1 g of a crude product of methyl 8-phthalimidooctyl 2,6-dimethyl-4-(m-nitrophenyl)-1,4-dihydropyridine-3,5-dicarboxylate.

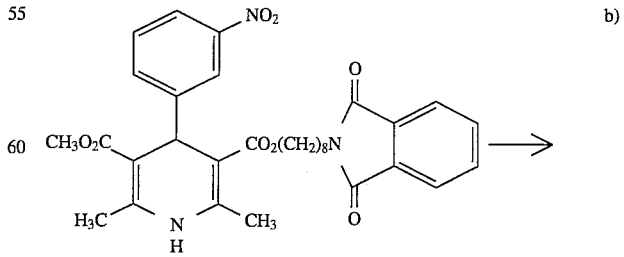

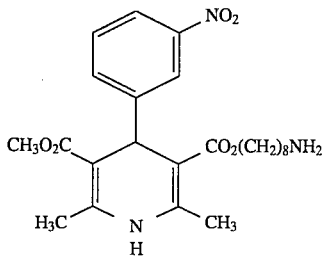

A solution of 16 g of methyl 8-phthalimidooctyl 2,6-dimethyl-4-(m-nitrophenyl)-1,4-dihydropyridine-3,5-dicarboxylate and 6.8 g of hydrazine monohydrate in 160 ml of ethanol was refluxed for 2 hours under heating. Precipitates (solid) thus formed was removed by filtration. The filtrate was concentrated under reduced pressure and after adding chloroform to the residue, precipitates again removed by filtration. The filtrate was concentrated under reduced pressure, and the residue was subjected to silica gel column chromatography. The product was eluted with chloroform-methanol (8:2 v/v), and crude crystals were recrystallized from ethanol—petroleum ether to provide 6 g of 8-aminooctyl methyl 2,6-dimethyl-4-(m-nitrophenyl)-1,4-dihydropyridine-3,5-dicarboxylate.

Melting point: 133°–134° C.

Elemental analysis for $C_{24}H_{33}N_3O_6$

|  | C(%) | H(%) | N(%) |
|---|---|---|---|
| Calculated: | 62.73 | 7.24 | 9.14 |
| Found: | 62.54 | 7.45 | 9.07 |

EXAMPLE 2

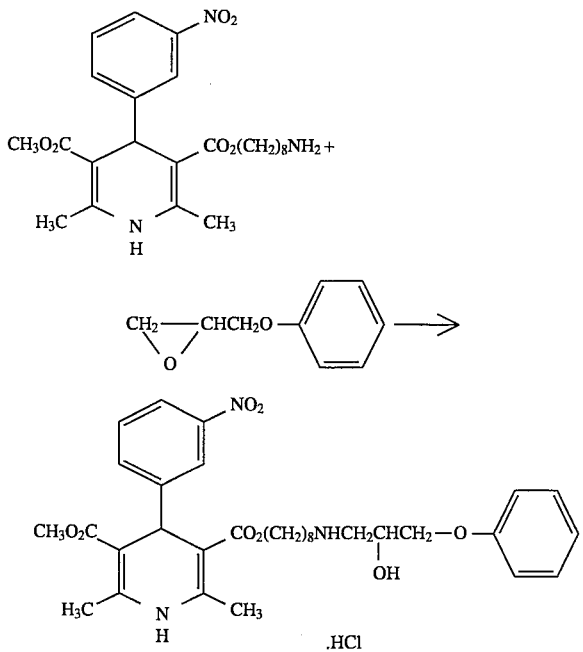

In 50 ml of ethanol were dissolved 3 g of 8-aminooctyl methyl 2,6-dimethyl-4-(m-nitrophenyl)-1,4-dihydropyridine-3,5-dicarboxylate and 1 g of glycidyl phenyl ether, and the mixture was stirred at room temperature for 20 hours, After the reaction mixture was concentrated under reduced pressure, the residue was subjected to silica gel column chromatography and the product was eluted with chloroform-methanol (95.5 v/v). 3.3 g of pale yellow powder of 8-(2-hydroxy-3-phenoxypropylamino)octyl methyl 2,6-dimethyl-4-(m-nitrophenyl)-1,4-dihydropyridine-3,5-dicarboxylate was obtained. The product was treated with an ethanol solution of hydrogen chloride to obtain 3 g of hydrochloric acid salt as amorphous powder.

Elemental analysis for $C_{33}H_{43}N_3O_3$ HCl 0.2 $H_2O$

|  | C(%) | H(%) | N(%) | Cl(%) |
|---|---|---|---|---|
| Calculated | 61.00 | 6.89 | 6.47 | 5.46 |
| Found: | 60.91 | 7.11 | 6.45 | 5.44 |

NMR (CDCl$_3$) (free compound) 2.36 (6H, s), 2.68 (2H, s), 3.66 (3H, s), 5.12 (1H, s), 6.40 (1H, s).

EXAMPLE 3

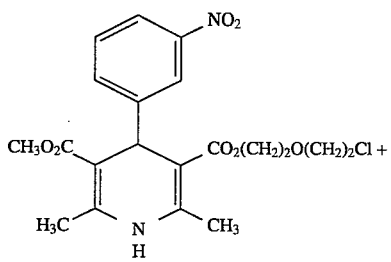

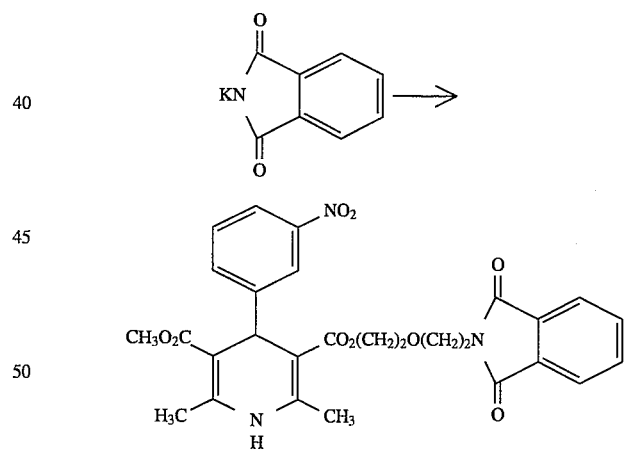

In 10 ml of N,N-dimethylformamide was dissolved 7.3 of 2-(2-chloroethoxy)ethyl methyl 2,6-dimethyl-4-(m-nitrophenyl)-1,4-dihydropyridine-3,5-dicarboxylate and 3.4 g of potassium phthalimide, and the mixture was heated at 140°–150° C. for 3 hours. After cooling the mixture to room temperature and then adding thereto water, precipitates were extracted with chloroform. The extract was washed with a saturated aqueous sodium chloride, and concentrated under reduced pressure to provide 9.14 g of crude product of methyl 2-(2-phthalimidoethoxy)ethyl 2,6-dimethyl-4-(m-nitrophenyl)-1,4-dihydropyridine-3,5-dicarboxylate.

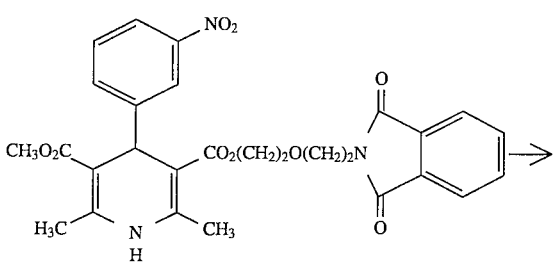

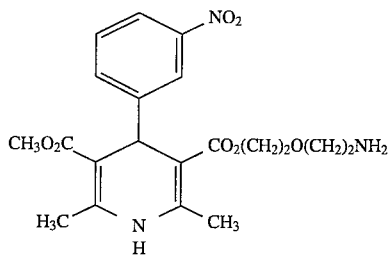

A solution of 9.14 g of methyl 2-(2-phthalimidoethoxy)ethyl 2,6-dimethyl-4-(m-nitrophenyl)-1,4-dihydropyridine-3,5-dicarboxylate and 4,2 g of hydrazine monohydrate in 100 ml of ethanol was refluxed for 2 hours under heating. After cooling the reaction solution with ice and then adding thereto 100 ml of chloroform, precipitates were removed by filtration. The filtrate was concentrated under reduced pressure, and the residue was subjected to silica gel column chromatography. The product was eluted with chloroform-methanol (8:2 v/v) and 4.8 g of 2-(2-aminoethoxy)ethyl methyl 2,6-dimethyl-4-(m-nitrophenyl)-1,4-dihydropyridine-3,5-dicarboxylate was obtained as liquid.

NMR (CDCl$_3$) δ: 2.36 (3H, s), 2.86 (2H, t), 3.66 (3H, s), 4.24 (2H, t), 5.12 (1H, s), 6.50 (1H, s).

EXAMPLE 4

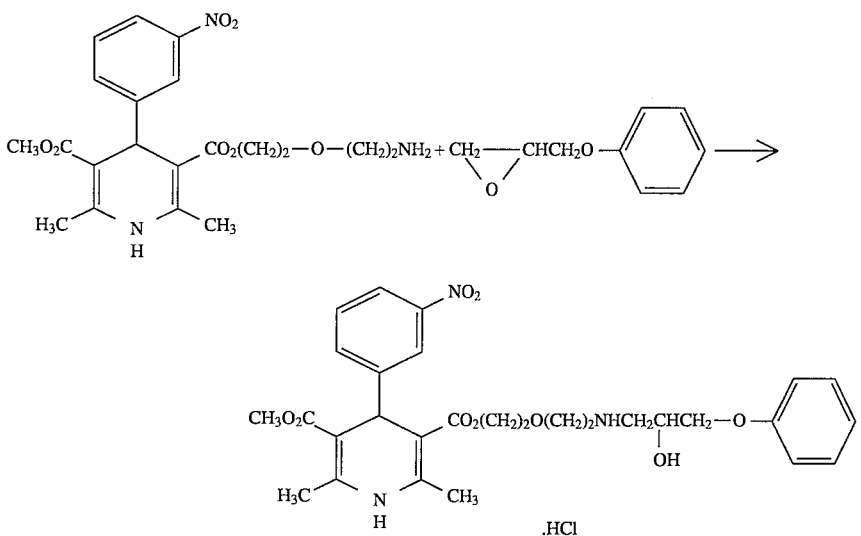

In 20 ml of ethanol were dissolved 1.8 g of 2-(2-aminoethoxy)ethyl methyl 2,6-dimethyl-4-(m-nitrophenyl)- 1,4-dihydropyridine-3,5-dicarboxylate and 0.64 g of glycidyl phenyl ether, and the solution was stirred at room temperature for 20 hours. The reaction solution was concentrated under reduced pressure and the residue was subjected to silica gel column chromatography. The product was eluted with chloroform-methanol (95.5 v/v), and 0.87 g of 2-[2-(2-hydroxy-3-phenoxypropylamino)ethoxy]ethyl methyl 2,6-dimethyl-4-(m-nitrophenyl)-1,4-dihydropyridine-3,5-dicarboxylate was obtained. The product was treated with an ethanol solution of hydrochloric acid to provide 0.8 g of hydrochloric acid salt as amorphous powder.

Elemental analysis for $C_{29}H_{35}N_3O_9$ HCl 0.4 $H_2O$

|  | C(%) | H(%) | N(%) | Cl(%) |
| --- | --- | --- | --- | --- |
| Calculated: | 56.80 | 6.05 | 6.85 | 5.78 |
| Found: | 56.82 | 6.11 | 6.74 | 5.99 |

NMR (CDCl$_3$) (free compound) δ: 2.36 (6H, s), 2.68–3.08 (4H), 3.64 (3H, s), 3.80–4.40 (5H), 5.12 (1H, s), 5.94 (1H, s).

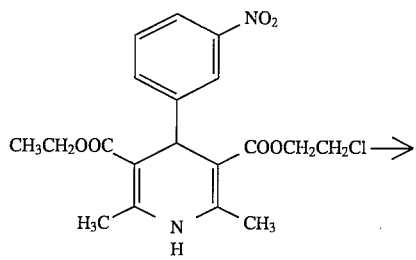

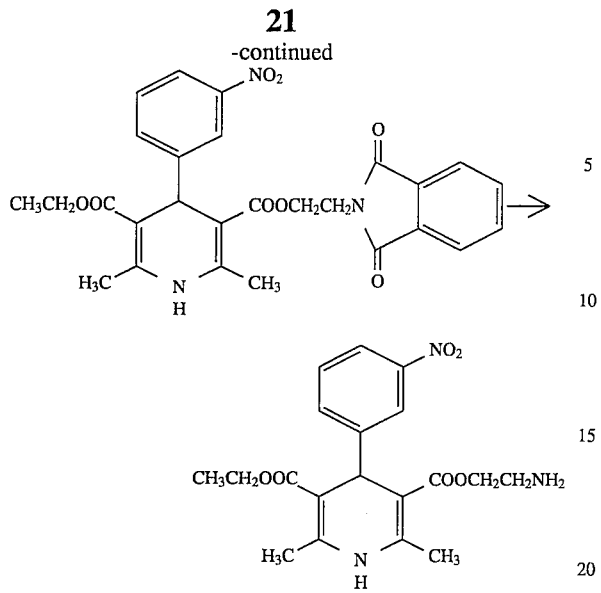

a) In 30 ml of N,N-dimethylformamide were dissolved 18.4 g of 2-chloroethyl ethyl 2,6-dimethyl-4-(m-nitrophenyl)-1,4-dihydropyridin-3,5-dicarboxylate and 8.4 g of potassium phthalimide, and the solution was heated for 3 hours at 120°–130° C. The reaction mixture was poured into 1000 ml of ice-water, and precipitated crystals were collected by filtration. The crystals were recrystallized from ether-ethyl acetate to provide 17 g of 2,6-dimethyl-4-(m-nitrophenyl)-1,4-dihydropyridin-3,5-dicarboxylate. Melting point: 168°–171° C.

b) A solution of 17 g of ethyl 2-phthalimidoethyl 2,6-dimethyl-4-(m-nitrophenyl)-1,4-dihydropyridine-3,5-dicarboxylate and 8 ml of hydrazine monohydrate in 170 ml of ethanol was refluxed under heating for 30 minutes.

Precipitated crystals were removed by filtration at hot state, and the filtrate was concentrated under reduced pressure to remove the solvent. After adding water to the residue, the product was extracted with ethyl acetate, and the extract was washed with water, dried over anhydrous sodium sulfate, and concentrated to remove the the solvent. Crude crystal thus obtained were recrystallized from ethanol to provide 6.5 g of 2-aminoethyl ethyl 2,6-dimethyl-4-(m-nitrophenyl)-1,4-dihydropyridine-3,5-dicarboxylate.

Melting point: 137°–139° C.

Elemental analysis for $C_{19}H_{23}N_3O_6$

|  | C(%) | H(%) | N(%) |
| --- | --- | --- | --- |
| Calculated: | 58.60 | 5.95 | 10.79 |
| Found: | 58.42 | 6.05 | 10.79 |

NMR ($CDCl_3$) δ: 1.20 (3H, t), 2.32 (6H, s), 2.86 (2H, t), 4.08 (2H, q), 5.08 (1H, s), 5.84 (1H, s).

EXAMPLE 6

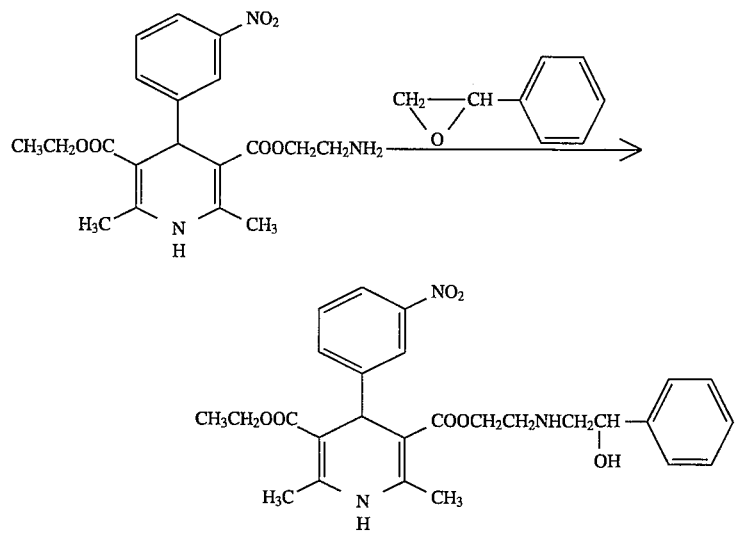

In 25 ml of methanol was dissolved 1.95 g of 2-aminoethyl ethyl 2,6-dimethyl-4-(m-nitrophenyl)-1,4-dihydropyridine-3,5-dicarboxylate and after adding thereto 0.6 g of stylene oxide the mixture was allowed to stand for 2 days at room temperature. The solvent was distilled off under reduced pressure, and the residue was subjected to column chromatography on silicagel (100 g) and the product was eluted with chloroform-methanol (98:2 v/v). Crude crystals were recrystallized from ethyl acetate, and 300 mg of ethyl 2-(β-hydroxyphenetylamino)ethyl 2,6-dimethyl-4-m-nitrophenyl)-1,4-dihydropyridine-3,5-dicarboxylate was obtained.

Melting point: 108°–109° C.

Elemental analysis for $C_{27}H_{31}N_3O_7$

| | C(%) | H(%) | N(%) |
|---|---|---|---|
| Calculated: | 63.64 | 6.13 | 8.25 |
| Found: | 63.58 | 6.28 | 8.24 |

NMR (CDCl$_3$) δ: 1.22 (3H, t), 2.36 (6H, s), 4.66 (1H, m) 5.10 (1H, s), 6.12 (1H, s).

EXAMPLE 7

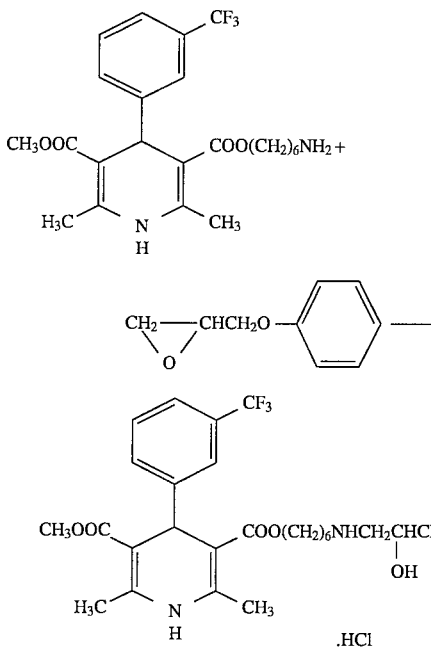

In 45 ml of methanol were dissolved 2.51 g of 6-aminohexyl methyl 2,6-dimethyl-4-(m-trifluoromethylphenyl)-1,4-dihydropyridine-3,5-dicarboxylate and 0.83 g of glycidyl phenyl ether, and the mixture was stirred for 45 hours at room temperature. The reaction solution was concentrated under reduced pressure, and the residue was subjected to silica gel column chromatography. The produce was eluted with chloroform-methanol (95:5 v/v), and 1.10 g of 6-(2-hydroxy-3-phenoxypropylamino)hexyl methyl 2,6-dimethyl-4-(m-trifluoromethylphenyl)-1,4-dihydropyridin-3,5-dicarboxylate was obtained. This product was treated with an ethanol solution of hydrogen chloride to obtain amorphous powder of 1.16 g of hydrochloric acid salt.

Elemental analysis for $C_{32}H_{39}N_2O_6F_3 \cdot HCl \cdot H_2O$

| | C(%) | H(%) | N(%) | F(%) | Cl(%) |
|---|---|---|---|---|---|
| Calculated: | 58.31 | 6.42 | 4.25 | 8.65 | 5.38 |
| Found: | 58.25 | 6.44 | 4.22 | 8.57 | 5.52 |

NMR (CDCl$_3$) (free compound) δ: 2.32 (3H, s), 2,34 (3H, s), 3.64 (3H, s), 5.05 (1H, s), 6.00 (1H, s).

By following the same procedure as in Examples 1 to 7, the following compounds were obtained.

In the following examples, mp, Anal, NMR, Cal and Fond are abbreviations for melting point, elementary analysis values, nuclear magnetic resonance spectrum, calculated and found. (By following the same procedure as in Exs. 1, 3 and 5, the following compounds were obtained.)

Example 8

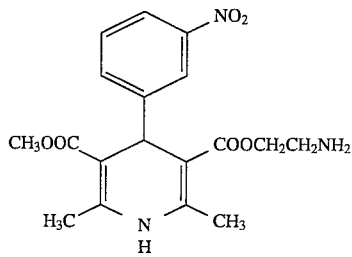

2-aminoethyl methyl 2,6-di-methyl-4-(m-nitrophenyl)-1,4-dihydropyridine-3,5-dicarboxylate
(I) mp 149–150° C.
(II) Anal ($C_{18}H_{21}N_3O_2$)

| | C (%), | H (%), | N (%) |
|---|---|---|---|
| Cal | 57.59 | 5.64 | 11.19 |
| Fnd | 57.35 | 5.68 | 11.17 |

(III) NMR (CDCl$_3$)
δ: 2.34 (6H, s)
2.90 (2H, t)
3.64 (3H, s)
5.08 (1H, s)
6.68 (1H, s)

Example 9

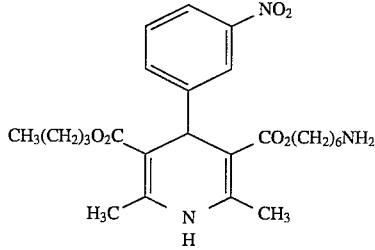

6-aminohexyl decyl 2,6-dimethyl-4-(m-nitrophenyl)-1,4-(dihydropyradine-3,5-dicarboxylate
(I) amorphous powder
(II) Anal ($C_{31}H_{37}N_3C_5O$. 0.5 H$_2$O)

| | C (%), | H (%), | N (%) |
|---|---|---|---|
| Cal | 65.70 | 8.54 | 7.41 |
| Fnd | 65.60 | 8.60 | 7.55 |

(III) NMT (CDCl$_3$)
δ: 0.88 (3H, t)
2.36 (6H, s)
2.68 (2H, t)
4.04 (4H, t)
5.12 (1H, s)
6.20 (1H, s)

(By following the same procedure as in Examples 2, 4, 6, and 7. the following compounds were obtained.)

Example 10

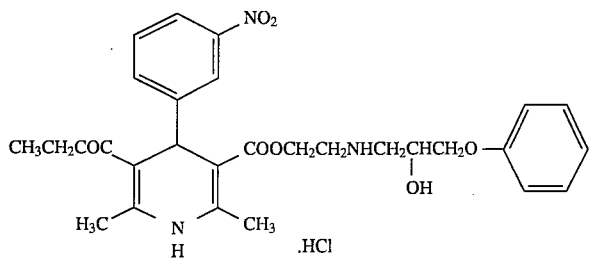

Ethyl 2-(2-hydroxy-3-phenoxypropylamino)ethyl 2,6-dimethyl-4-(m-nitro-phenyl)-1,4-dihydropyridine-3,5-dicarboxylate hydrochloride
(I) 187~190° C.
(II) Anal ($C_{23}H_{31}N_3O_4$·HCl)

|  | C (%), | H (%), | N (%), | Cl (%) |
|---|---|---|---|---|
| Cal | 58.38 | 5.95 | 7.29 | 6.15 |
| Fnd | 58.12 | 5.98 | 7.23 | 6.43 |

(III) NMR ($d_6$-DMSO)
δ: 1.12 (3H, t)
2.34 (6H, s)
3.8~4.4 (8H, m)
5.04 (1H, s)

Example 11

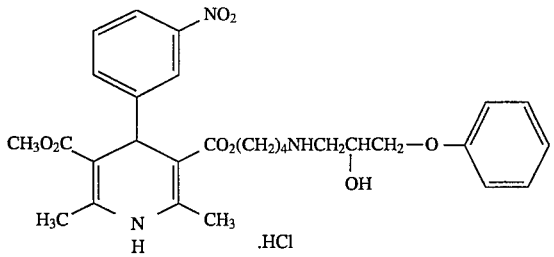

4-(2-hydroxy-3-phenoxy-propylamino)butyl methyl 2,6-dimethyl-4-(m-nitro-phenyl)-1,4-dihydropyridine-3,5-dicarboxylate hydrochloride
(I) amorphous powder
(II) Anal ($C_{27}H_{35}N_3O_4$·HCl 0.6 $H_2O$)

|  | C (%), | H (%), | N (%) |
|---|---|---|---|
| Cal | 57.97 | 6.24 | 6.99 |
| Fnd | 57.88 | 6.38 | 6.99 |

(III) NMR (CDCl$_3$)
(free form)
δ: 1.20~1.90 (4H, m)
2.36 (3H, s)
2.38 (3H, s)
3.66 (3H, s)
5.12 (1H, s)
5.94 (1H, s)

Example 12

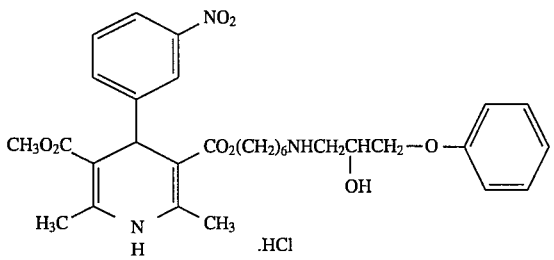

6-(2-hydroxy-3-phenoxy-propylamino)hexyl methyl 2,6-dimethyl-4-(m-nitro-phenyl)-1,4-dihydropyridine-3,5-dicarboxylate hydrochloride
(I) mp 117~119° C.
(II) Anal ($C_{31}H_{39}N_3O_6$·HCl)

|  | C (%), | H (%), | N (%), | Cl (%) |
|---|---|---|---|---|
| Cal | 60.24 | 6.52 | 6.80 | 5.74 |
| Fnd | 59.91 | 6.68 | 6.66 | 6.08 |

(III) NMR (CDCl$_3$)
(free form)
δ: 1.08~1.80 (8H, m)

| | |
|---|---|
| 2.36 | (3H, s) |
| 2.38 | (3H, s) |
| 3.66 | (3H, s) |
| 5.12 | (1H, s) |
| 5.85 | (1H, s) |

Example 13

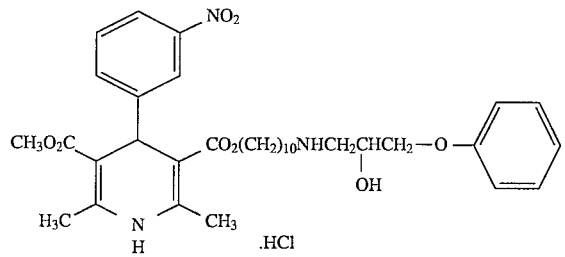

10-(2-hydroxy-3-phenoxy-propylamino)decyl methyl 2,6-dimethyl-4-(m-nitro-phenyl)-1,4-dihydropyridine-3,5-dicarboxylate hydrochloride
(I) amorphous powder
(II) Anal ($C_{35}H_{47}N_3O_4 \cdot HCl$)

| | C (%), | H (%), | N (%), | Cl (%) |
|---|---|---|---|---|
| Cal | 62.35 | 7.18 | 6.23 | 5.26 |
| Fnd | 62.47 | 7.17 | 6.17 | 5.39 |

(III) NMR (CDCl$_3$)
(free form)

| δ: | 1.00~1.80 | (16H, m) |
|---|---|---|
| | 2.36 | (3H, s) |
| | 2.38 | (3H, s) |
| | 3.66 | (3H, s) |
| | 5.12 | (1H, s) |
| | 5.94 | (1H, s) |

Example 14

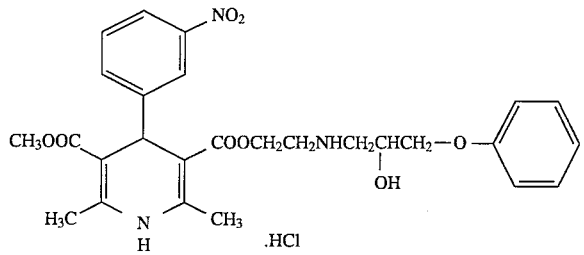

2-(2-hydroxy-3-phenoxy-propylamino)ethyl methyl 2,6-dimethyl-4-(m-nitro-phenyl)-1,4-dihydropyridine-3,5-dicarboxylate hydrochloride
(I) mp 164~166° C.
(II) Anal ($C_{27}H_{31}N_3O_4 \cdot HCl$)

| | C (%), | H (%), | N (%), | Cl (%) |
|---|---|---|---|---|
| Cal | 57.70 | 5.74 | 7.48 | 6.31 |
| Fnd | 57.59 | 5.78 | 7.47 | 6.35 |

(III) NMR (CDCl$_3$)
(free form)

| δ: | 2.36 (6H, s) |
|---|---|
| | 3.64 (3H, s) |
| | 3.88~4.46 (5H, m) |
| | 5.08 (1H, s) |
| | 5.78 (1H, s) |

Example 15

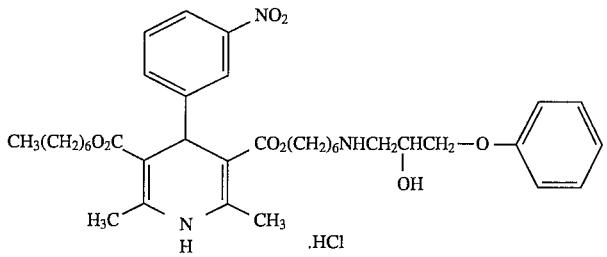

Decyl 6-(2-hydroxy-3-phenoxypropylamino)hexyl 2,6-dimethyl-4-(m-nitro-phenyl)1,4-dihydropyridine-3,5-dicarboxylate hydrochloide -continued (I) amorphous powder
(II) Anal (C₄₀H₅₇N₃O₄·HCl)

|     | C (%) | H (%) | N (%) | Cl (%) |
|-----|-------|-------|-------|--------|
| Cal | 64.54 | 7.85  | 5.65  | 4.76   |
| Fnd | 64.57 | 8.12  | 5.76  | 5.09   |

(III) NMR (CDCl₃)
(free form)
δ: 0.88 (3H, t)
2.36 (6H, s)
2.64 (2H, t)
5.10 (1H, s)
5.88 (1H, s)

Example 16

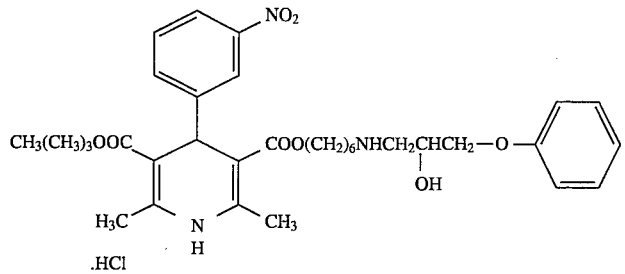

Butyl 6-(2-hydroxy-3-phenoxypropylamino)-hexyl 2,6-dimethyl-4-(m-nitrophenyl)-1,4-di-hydroxypyridine-3,5-dicarboxylate hydrochloride
(I) amorphous powder
(II) Anal (C₃₆H₄₅N₃O₆·HCl)

|     | C (%) | H (%) | N (%) | Cl (%) |
|-----|-------|-------|-------|--------|
| Cal | 61.86 | 7.02  | 6.36  | 5.37   |
| Fnd | 61.74 | 7.18  | 6.22  | 5.49   |

(III) NMR (CDCl₃)
(free form)
δ: 0.88 (3H, t)
2.34 (6H, s)
5.10 (1H, s)
5.82 (1H, s)

Example 17

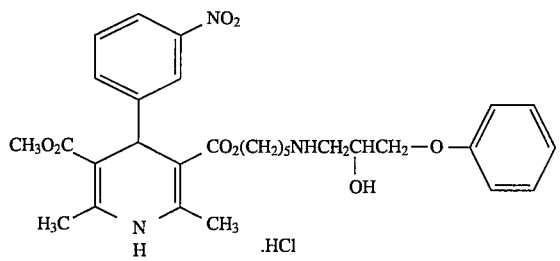

5-(2-hydroxy-3-phenoxy-propylamino)pentyl methyl 2,6-dimethyl-4-(m-nitro-phenyl)-1,4-dihydro-pyridine-3,5-dicarboxylate hydrochloride
(I) amorphous powder
(II) Anal (C₃₀H₃₇N₃O₅·HCl)

|     | C (%) | H (%) | N (%) |
|-----|-------|-------|-------|
| Cal | 59.65 | 6.34  | 6.96  |
| Fnd | 59.62 | 6.43  | 7.11  |

(III) NMR (CDCl₃)
(free form)
δ: 2.35 (6H, s)
3.64 (3H, s)
4.00 (2H, s)
5.10 (1H, s)

Example 18

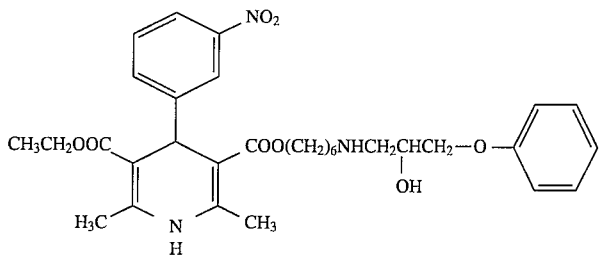

Ethyl 6-(2-hydroxy-3-phenoxy/propylamino)hexyl 2,6-dimethyl-4-(m-nitrophenyl)-1,4-dihydroxypyridine-3,5-dicarboxylate
(I)  amorphous powder
(II) Anal ($C_{32}H_{41}N_3O_8 \cdot 0.2H_2O$)

|  | C (%) | H (%) | N (%) |
|---|---|---|---|
| Cal | 64.13 | 6.96 | 7.01 |
| Fnd | 64.05 | 7.11 | 6.84 |

(III) NMR (CDCl$_3$)
(free form)
δ: 2.34 (6H, s)
5.10 (1H, s)
5.97 (1H, s)

Example 19

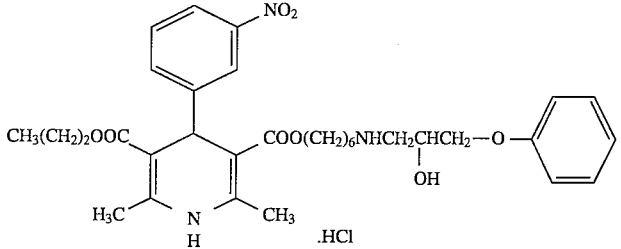

6-(2-hydroxy-3-phenoxy-propylamino)hexyl propyl 2,6-dimethyl-4-(m-nitro-phenyl)-1,4-dihydro-pyridine-3,5-dicarboxylate hydrochloride
(I)  amorphous powder
(II) Anal ($C_{33}H_{43}N_3O_6 \cdot HCl$)

|  | C (%) | H (%) | N (%) |
|---|---|---|---|
| Cal | 61.34 | 6.86 | 6.50 |
| Fnd | 61.06 | 6.69 | 6.42 |

(III) NMR (CDCl$_3$)
(free form)
δ: 0.88 (3H, t)
2.34 (6H, s)
3.78~4.28 (9H, m)
5.10 (1H, s)

Example 20

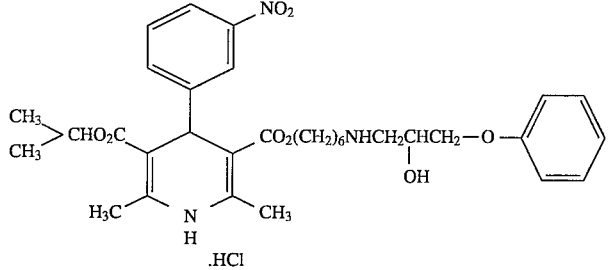

6-(2-hydroxy-3-phenoxy-propylamino)hexyl isopropyl 2,6-dimethyl-4-(m-nitrophenyl)-1,4-dihydropyridine-3,5-dicarboxylate hydrochloride
(I)  Amourphous powder
(II) Anal ($C_{33}H_{43}N_3O_6 \cdot HCl \cdot \frac{1}{2}H_2O$)

|  | C (%) | H (%) | N (%) |
|---|---|---|---|
| Cal | 60.50 | 6.92 | 6.41 |
| Fnd | 60.30 | 6.98 | 6.38 |

(III) NMR (CDCl$_3$)
(free form)
δ: 2.34 (6H, s)

| | |
|---|---|
| 2.62 (2H, t) | |
| 5.08 (1H, s) | |

Example 21

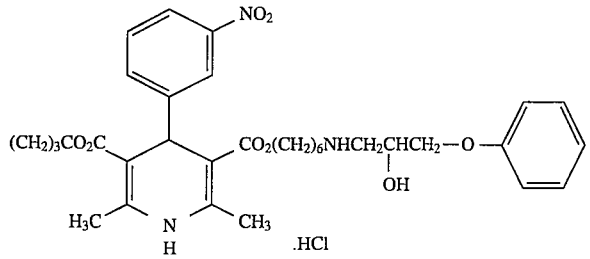

tert-butyl 6-(2-hydroxy-3-phenoxypropylamino)hexyl 2,6-dimethyl-4-(m-nitrophenyl)-1,4-dihydropyridine-3,5-dicarboxylate hydrochloride
(I)  amorphous powder
(II) Anal ($C_{36}H_{45}N_3O_6 \cdot HCl \cdot H_2O$)

| | C (%), | H (%), | N (%) |
|---|---|---|---|
| Cal | 60.21 | 7.13 | 6.20 |
| Fnd | 60.38 | 7.16 | 6.36 |

(III) NMR    (CDCl$_3$)
  (free form)
  δ:  1.40 (0H, s)
    2.30 (3H, s)
    2.34 (3H, s)
    2.62 (2H, t)
    5.04 (1H, s)

Example 22

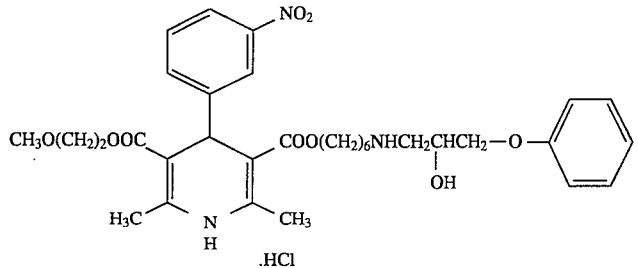

6-(2-hydroxy-3-phenoxy-propylamino)hexyl 2-methoxyethyl-2,6-dimethyl-4-(m-nitrophenyl-3,5-dicarboxylate hydrochloride
(I)  amorphous powder
(II) Anal ($C_{33}H_{43}N_3O_6 \cdot HCl$)

| | C (%), | H (%), | N (%) |
|---|---|---|---|
| Cal | 59.86 | 6.70 | 6.35 |
| Fnd | 59.71 | 6.83 | 6.29 |

(III) NMR    (CDCl$_3$)
  (free form)
  δ:  2.34 (6H, s)
    2.64 (2H, t)
    3.32 (3H, s)
    5.11 (1H, s)

Example 23

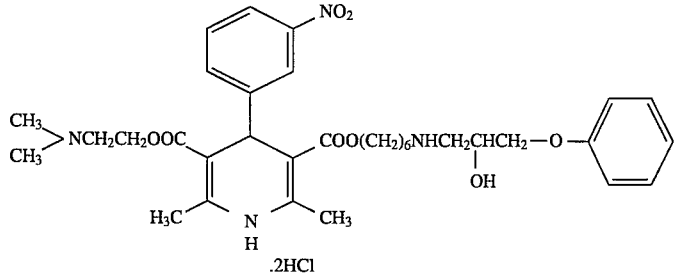

6-(2-hydroxy-3-phenoxy-propylamino)hexyl 2-dimethylaminoethyl 2,6-dimethyl-4-(m-nitrophenyl)-1,4-dihydropyridine-3,5-dicarboxylate dihydrochloride
(I)  amorphous powder
(II) Anal ($C_{34}H_{46}N_4O_3 \cdot 2HCl \cdot 1.8H_2O$)

| | C (%), | H (%), | N (%), | Cl (%) |
|---|---|---|---|---|

| | | | | |
|---|---|---|---|---|
| Cal | | 54.88 | 6.99 | 7.53 | 9.53 |
| Fnd | | 54.90 | 6.90 | 7.50 | 9.73 |
| (III) | NMR | (CDCl₃) | | | |
| | (free form) | | | | |
| | δ: 2.23 (6H, s) | | | | |
| | 2.36 (6H, s) | | | | |
| | 5.12 (1H, s) | | | | |
| | 5.79 (1H, s) | | | | |

Example 24

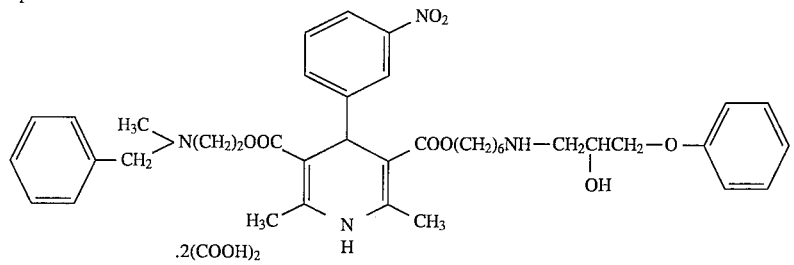

2-(N-benzyl-N-methylamino)-ethyl 6-(2-hydroxy-3-phenoxypropylamino)hexyl 2,6-dimethyl-4-(m-nitrophenyl)-1,4-dihydropyridine-3,5-dicarboxylate dioxalic acid salt
(I)  amorphous powder
(II) Anal ($C_{40}H_{50}N_4O_8 \cdot 2(COOH)_2$)

| | C (%), | H (%), | N (%) |
|---|---|---|---|
| Cal | 59.05 | 6.08 | 6.26 |
| Fnd | 58.69 | 6.14 | 6.18 |

(III) NMR (CDCl₃)
(free form)
δ:  2.16 (3H, s)
    2.34 (6H, s)
    2.64 (2H, t)
    3.50 (2H, s)
    4.16 (2H, t)
    5.10 (1H, s)

Example 25

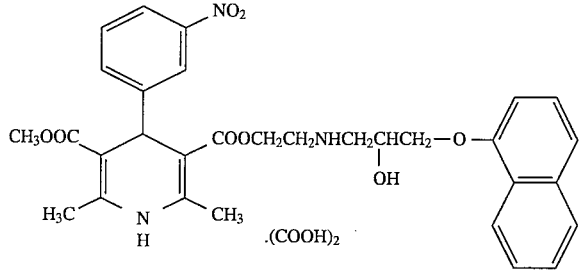

2-[2-hydroxy-3-(1-naphthoxy)propylamino]ethyl methyl 2,6-dimethyl-4-(m-nitrophenyl)-1,4-dihydropyridine-3,5-dicarboxylate oxalic acid salt
(I)  mp 146~149° C.
(II) Anal ($C_{31}H_{33}N_3O_8 \cdot (COOH)_2$)

| | C (%), | H (%), | N (%) |
|---|---|---|---|
| Cal | 59.55 | 5.30 | 6.31 |
| Fnd | 59.16 | 5.29 | 6.37 |

(III) NMR (d₆-DMSO)
δ:  2.14 (3H, s)
    2.30 (3H, s)
    3.62 (3H, s)
    5.08 (1H, s)

Example 26

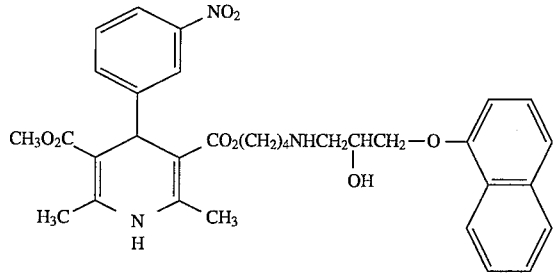

4-[2-hydroxy-3-(1-naphthyloxy)propylamino]butyl methyl 2,6-dimethyl-4-(m-nitrophenyl)-1,4-dihydropyridine-3,5-dicarboxylate
(I) amorphous powder
(II) Anal ($C_{33}H_{37}N_3O_6$)

|     | C (%) | H (%) | N (%) |
|-----|-------|-------|-------|
| Cal | 65.66 | 6.18  | 6.96  |
| Fnd | 65.62 | 6.41  | 6.61  |

(III) NMR (CDCl$_3$)
δ: 2.32 (6H, s)
3.62 (3H, s)
5.10 (1H, s)
6.84 (1H, dd)

Example 27

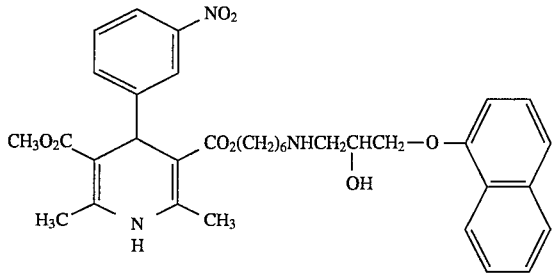

6-[2-hydroxy-3-(1-naphthyloxy)propylamino]hexyl methyl 2,6-dimethyl-4-(m-nitrophenyl)-1,4-dihydropyridine-3,5-dicarboxylate
(I) amorphous powder
(II) Anal ($C_{35}H_{41}N_3O_8$)

|     | C (%) | H (%) | N (%) |
|-----|-------|-------|-------|
| Cal | 66.55 | 6.54  | 6.65  |
| Fnd | 66.39 | 6.25  | 6.51  |

(III) NMR (CDCl$_3$)
δ: 2.34 (6H, s)
3.64 (3H, s)
5.10 (1H, s)
6.84 (1H, dd)

Example 28

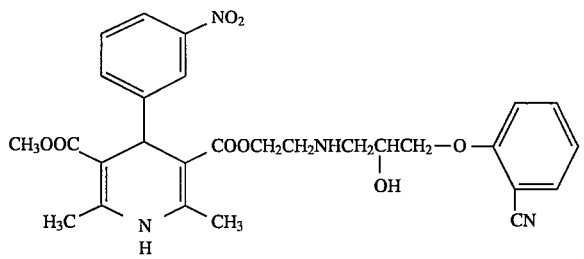

2-[3-(o-cyanophenoxy)-2-hydroxypropylamino]ethyl methyl 2,6-dimethyl-4-(m-nitrophenyl)-1,4-dihydropyridine-3,5-dicarboxylate
(I) 152~155° C.
(II) ($C_{28}H_{30}N_4O_6$)

|     | C (%) | H (%) | N (%) |
|-----|-------|-------|-------|
| Cal | 61.08 | 5.49  | 10.18 |
| Fnd | 60.76 | 5.31  | 10.09 |

(III) NMR (CDCl$_3$)
δ: 2.32 (3H, s)
2.36 (3H, s)
3.64 (3H, s)
5.10 (1H, s)

Example 29

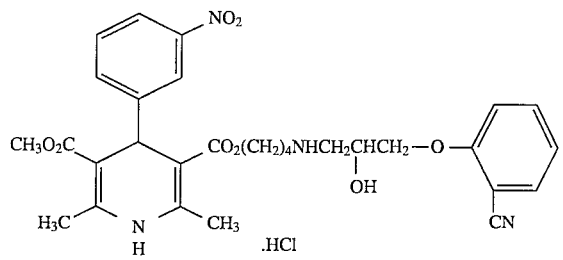

4-[3-(o-cyanophenoxy)-2-hydroxypropylamino]butyl methyl 2,6-dimethyl-4-(m-nitrophenyl)-1,4-dihydropyridine-3,5-dicarboxylate hydrochloride
(I) amorphous powder
(II) Anal ($C_{30}H_{34}N_4O_6 \cdot HCl$)

|  | C (%), | H (%), | N (%) |
|---|---|---|---|
| Cal | 58.58 | 5.74 | 9.11 |
| Fnd | 58.68 | 5.71 | 9.05 |

(III) NMR (CDCl$_3$)
(free form)
δ: 3.34 (6H, s)
3.64 (3H, s)
4.10 (2H, s)
5.08 (1H, s)

Example 30

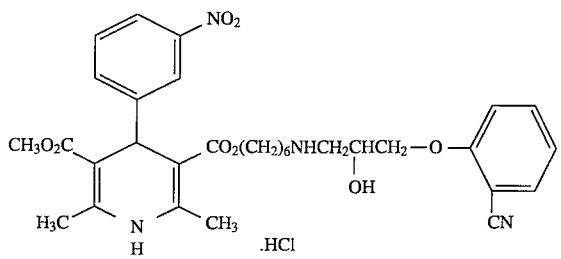

6-[3-(o-cyanophenoxy)-2-hydroxypropylamino]hexyl methyl 2,6-dimethyl-4-(m-nitrophenyl)-1,4-dihydropyridine-3,5-dicarboxylate hydrochloride
(I) amorphous powder
(II) Anal ($C_{32}H_{38}N_4O_8 \cdot HCl$)

|  | C (%), | H (%), | N (%) |
|---|---|---|---|
| Cal | 59.76 | 6.11 | 8.71 |
| Fnd | 59.97 | 5.93 | 8.83 |

(III) NMR (CDCl$_3$)
(free form)
δ: 2.32 (3H, s)
2.34 (3H, s)
3.60 (3H, s)
5.06 (1H, s)

Example 31

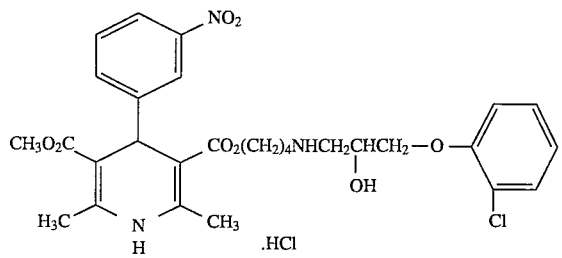

4-[3-(o-chlorophenoxy)-2-hydroxypropylamino]butyl methyl 2,6-dimethyl-4-(m-nitrophenyl)-1,4-dihydropyridine-3,5-dicarboxylate hydrochloride
(I) amorphous powder
(II) Anal ($C_{29}H_{34}ClN_3O_6 \cdot HCl$)

|  | C (%), | H (%), | N (%) |
|---|---|---|---|
| Cal | 55.77 | 5.65 | 6.73 |
| Fnd | 55.62 | 5.94 | 6.67 |

(III) NMR (CDCl$_3$)
(free form)
δ: 2.32 (6H, s)

2.64 (2H, t)
3.60 (3H, s)
5.06 (1H, s)

Example 32

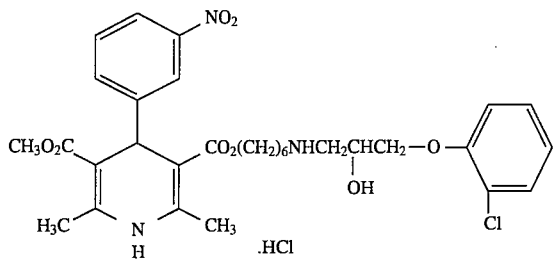

6-[3-(o-chlorophenoxy)-2-hydroxypropylamino]hexyl methyl 2,6-dimethyl-4-(m-nitrophenyl)-1,4-dihyrdopyridine-3,5-dicarboxylate hydrochloride
(I)     amorphous powder
(II)    Anal ($C_{31}H_{38}ClN_3O_8$.HCl)

|     | C (%) | H (%) | N (%) |
|-----|-------|-------|-------|
| Cal | 57.06 | 6.02  | 6.44  |
| Fnd | 56.89 | 6.29  | 6.50  |

(III)   NMR         ($CDCl_3$)
        (free form)
        δ:  2.34 (6H, s)
            3.64 (3H, s)
            4.08 (2H, s)
            5.10 (1H, s)

Example 33

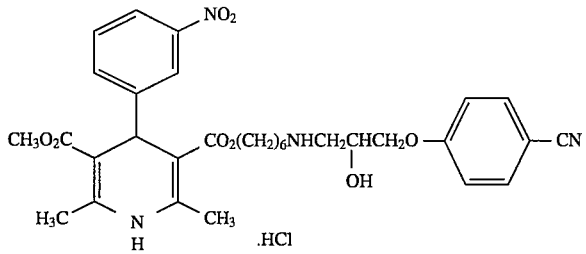

6-[3-(p-cyanophenoxy)-2-hydroxypropylamino]hexyl methyl 2,6-dimethyl-4-(m-nitrophenyl)-1,4-dihydropyridine-3,5-dicarboxylate hydrochloride
(I)     amorphous powder
(II)    Anal ($C_{32}H_{38}N_4O_8HCl.H_2O$)

|     | C (%) | H (%) | N (%) |
|-----|-------|-------|-------|
| Cal | 58.13 | 6.25  | 8.47  |
| Fnd | 58.44 | 6.37  | 8.29  |

(III)   NMR         ($CDCl_3$)
        (free form)
        δ:  2.34 (2H, s)
            2.36 (3H, s)
            2.64 (2H, t)
            3.64 (3H, s)
            5.10 (1H, s)

Example 34

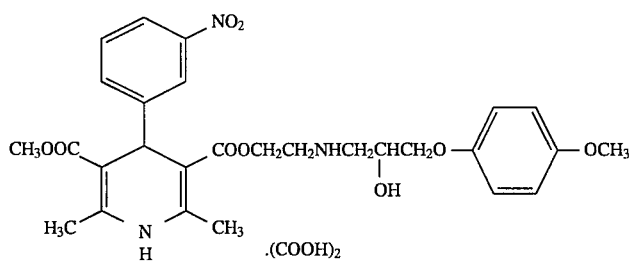

2-[2-hydroxy-3-(p-methoxyphenoxy)propylamino]ethyl methyl 2,6-dimethyl-4-(m-nitrophenyl)-1,4-dihydropyridine-3,5-dicarboxylate oxalic acid salt
(I)     mp 152–155° C.
(II)    Anal ($C_{28}H_{33}N_3O_8$.(COOH)$_2$)

|  | C (%) | H (%) | N (%) |
|--|-------|-------|-------|

|     |     |       |      |      |
|-----|-----|-------|------|------|
| Cal |     | 55.81 | 5.46 | 6.51 |
| Fnd |     | 55.43 | 5.43 | 6.48 |
| (III) | NMR | ($d_6$-DMSO) | | |
|     | δ: 2.32 (3H, s) | | | |
|     |     2.36 (3H, s) | | | |
|     |     3.64 (3H, s) | | | |
|     |     3.74 (3H, s) | | | |
|     |     5.08 (1H, s) | | | |

Example 35

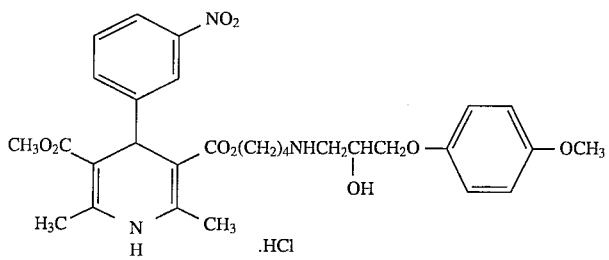

4-[2-hydroxy-3-(p-methoxyphenoxy)propylamino]butyl methyl 2,6-methyl-4-(m-nitrophenyl)-1,4-dihydropyridine-3,5-dicarboxylate hydrochloride
(I) amorphous powder
(II) Anal ($C_{30}H_{37}N_3O_9$·HCl)

|     |     | C (%) | H (%) | N (%) |
|-----|-----|-------|-------|-------|
| Cal |     | 58.11 | 6.18  | 6.78  |
| Fnd |     | 58.38 | 6.41  | 6.72  |
| (III) | NMR | ($CDCl_2$) | | |
|     | (free form) | | | |
|     | δ: 2.34 (6H, s) | | | |
|     |     3.64 (3H, s) | | | |
|     |     3.76 (3H, s) | | | |
|     |     5.10 (1H, s) | | | |

Example 36

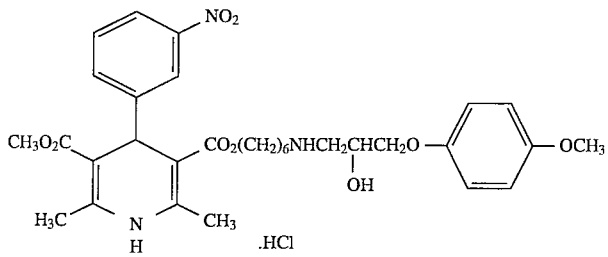

6-[2-hydroxy-3-(p-methoxyphenoxy)propylamino]hexyl methyl 2,6-dimethyl-4-(m-nitrophenyl)-1,4-dihydropyridine-3,5-dicarboxylate hydrochloride
(I) amorphous powder
(II) Anal ($C_{32}H_{41}N_3O_8$·HCl)

|     |     | C (%) | H (%) | N (%) |
|-----|-----|-------|-------|-------|
| Cal |     | 59.30 | 6.53  | 6.48  |
| Fnd |     | 59.23 | 6.89  | 6.61  |
| (III) | NMR | ($CDCl_3$) | | |
|     | (free form) | | | |
|     | δ: 2.36 (6H, s) | | | |
|     |     3.64 (3H, s) | | | |
|     |     3.76 (3H, s) | | | |
|     |     5.10 (1H, s) | | | |

Example 37

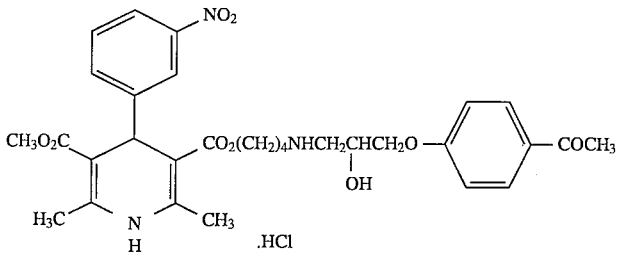

4-[3-(p-acetylphenoxy)-2-hydroxypropylamino]butyl methyl 2,6-dimethyl-4-(m-nitrophenyl)-1,4-dihyrdopyridine-3,5-dicarboxylate hydrochloride

|   |   |
|---|---|
| (I) | amorphous powder |
| (II) | Anal ($C_{31}H_{37}N_3O_8$·HCl) |

|  | C (%) | H (%) | N (%) |
|---|---|---|---|
| Cal | 58.90 | 6.06 | 6.65 |
| Fnd | 59.09 | 6.24 | 6.49 |

(III) NMR ($d_6$-DMSO)
δ: 2.32 (6H, s)
2.52 (3H, s)
3.56 (3H, s)
5.00 (1H, s)

Example 38

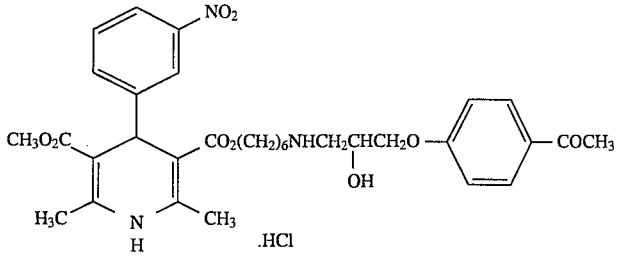

6-[3-(pacetylphenoxy)-2-hydroxypropylamino]hexyl methyl 2,6-dimethyl-4-(m-nitrophenyl)-1,4-dihydropyridine-3,5-dicarboxylate hydrochloride
(I) amorphous powder
(II) Anal ($C_{33}H_{41}N_3O_8$·HCl)

|  | C (%) | H (%) | N (%) |
|---|---|---|---|
| Cal | 60.04 | 6.41 | 6.37 |
| Fnd | 60.20 | 6.61 | 6.20 |

(III) NMR ($d_6$-DMSO)
δ: 2.28 (3H, s)
2.30 (3H, s)
2.52 (3H, s)
3.56 (3H, s)
5.00 (1H, s)

Example 39

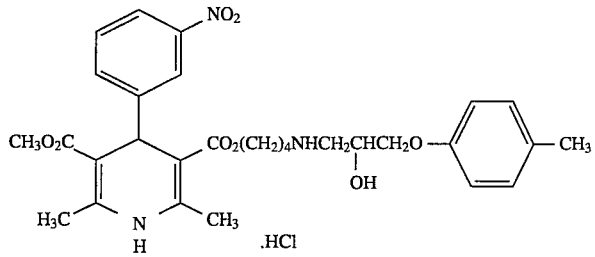

4-[2-hydroxy-3-(p-methylphenoxy)propylamino]butyl methyl 2,6-dimethyl-4-(m-nitrophenyl)-1,4-dihydropyridine-3,5-dicarboxylate hydrochloride
(I) amorphous powder
(II) Anal ($C_{30}H_{37}N_3O_6$·HCl·½$H_2O$)

|  | C (%) | H (%) | N (%) |
|---|---|---|---|
| Cal | 58.77 | 6.41 | 6.85 |
| Fnd | 58.52 | 6.74 | 6.78 |

(III) NMR ($CDCl_3$)
(free form)
δ: 2.28 (3H, s)
2.34 (6H, s)
3.64 (3H, s)
5.10 (1H, s)

Example 40

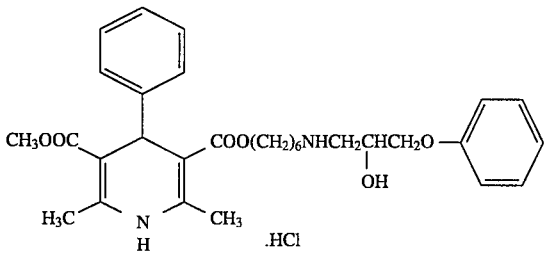

6-(2-hydroxy-3-phenoxypropylamino)hexyl methyl 2,6-dimethyl-4-phenyl-1,4-dihydropyridine-3,5-dicarboxylate hydrochloride
(I) amorphous powder
(II) Anal (C₃₁H₄₀N₂O₆·HCl·H₂O)

|     | C (%) | H (%) | N (%) |
|-----|-------|-------|-------|
| Cal | 62.99 | 7.33  | 4.74  |
| Fnd | 63.03 | 7.48  | 4.68  |

(III) NMR (CDCl₃)
(free form)
δ: 2.31 (3H, s)
2.33 (3H, s)
3.64 (3H, s)
5.00 (1H, s)
5.74 (1H, s)

Example 41

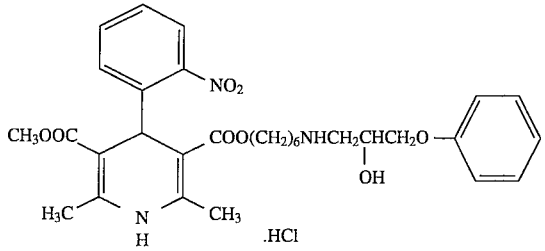

6-(2-hydroxy-3-phenoxypropylamino)hexyl methyl 2,6-dimethyl-4-(o-nitrophenyl)-1,4-dihydropyridine-3,5-dicarboxylate
(I) amorphous powder
(II) Anal (C₃₁H₃₉N₃O₈·0.5 H₂O)

|     | C (%) | H (%) | N (%) |
|-----|-------|-------|-------|
| Cal | 63.04 | 6.83  | 7.11  |
| Fnd | 63.12 | 6.69  | 7.12  |

(III) NMR (CDCl₃)
δ: 2.29 (3H, s)
2.34 (3H, s)
3.57 (3H, s)
5.77 (1H, s)
5.83 (1H, s)

Example 42

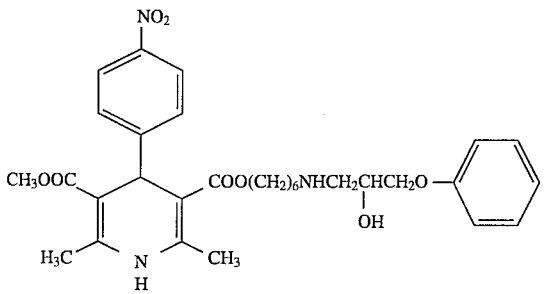

6-(2-hydroxy-3-phenoxypropylamino)hexyl methyl 2,6-dimethyl-4-(p-nitrophenyl)-1,4-dihydropyridine-3,5-dicarboxylate
(I) amorphous powder
(II) Anal (C₃₁H₃₉N₃O₈·0.5 H₂O)

|     | C (%) | H (%) | N (%) |
|-----|-------|-------|-------|
| Cal | 63.04 | 6.83  | 7.11  |
| Fnd | 62.90 | 7.02  | 6.99  |

(III) NMR (CDCl₃)
δ: 2.33 (3H, s)
2.36 (3H, s)
3.65 (3H, s)
5.10 (1H, s)
5.97 (1H, s)

-continued

Example 43

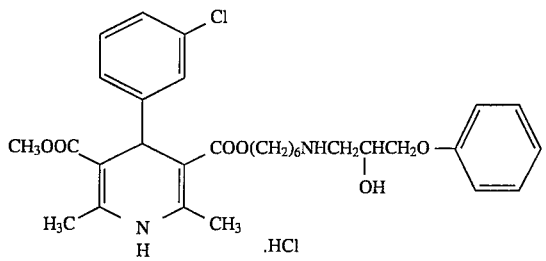

6-(2-hydroxy-3-phenoxypropylamino)hexyl methyl 4-(m-chlorophenyl)-2,6-dimethyl-1,4-dihydro-pyridine-3,5-dicarboxylate hydrochloride
(I)     amorphous powder
(II)    Anal ($C_{31}H_{38}N_2O_6Cl.HCl.0.7\ H_2O$)

|  | C (%) | H (%) | N (%) |
|---|---|---|---|
| Cal | 60.04 | 6.73 | 4.52 |
| Fnd | 60.03 | 6.79 | 4.43 |

(III)   NMR     (CDCl$_3$)
      (free form)
    δ:   2.31 (3H, s)
        2.34 (3H, s)
        3.66 (3H, s)
        4.98 (1H, s)
        6.04 (1H, s)

Example 44

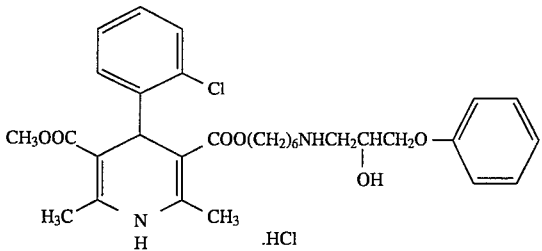

6-(2-hydroxy-3-phenoxypropylamino)hexyl methyl 4-(o-chlorophenyl)-2,6-dimethyl-1,4-dihydropyridine-3,5-dicarboxylate hydrochloride
(I)     amorphous powder
(II)    Anal ($C_{31}H_{38}N_2O_6Cl.HCl.H_2O$)

|  | C (%) | H (%) | N (%) |
|---|---|---|---|
| Cal | 59.52 | 6.77 | 4.48 |
| Fnd | 59.47 | 6.97 | 4.43 |

(III)   NMR     (CDCl$_3$)
      (free form)
    δ:   2.29 (3H, s)
        2.31 (3H, s)
        3.62 (3H, s)
        5.40 (1H, s)
        5.74 (1H, s)

Example 45

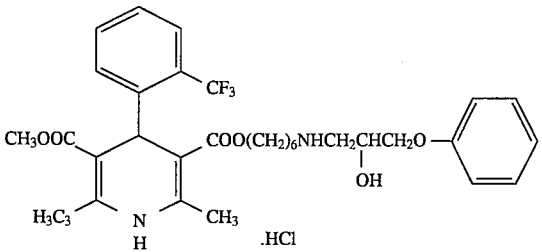

6-(2-hydroxy-3-phenoxypropylamino)hexyl methyl 2,6-dimethyl-3-(o-trifluoromethylphenyl)-1,4-dihydropyridine-3,5-dicarboxylate hydrochloride
(I)     amorphous powder
(II)    Anal ($C_{32}H_{39}N_2O_6F_3.HCl.H_2O$)

|  | C (%) | H (%) | N (%) |
|---|---|---|---|
| Cal | 58.31 | 6.42 | 4.25 |
| Fnd | 57.15 | 6.27 | 4.66 |

(III)   NMR     (CDCl$_3$)

|  |  |
|---|---|
| | (free form) |
| δ: | 2.28 (3H, s) |
| | 2.29 (3H, s) |
| | 3.58 (3H, s) |
| | 5.55 (1H, s) |
| | 5.96 (1H, s) |

Example 46

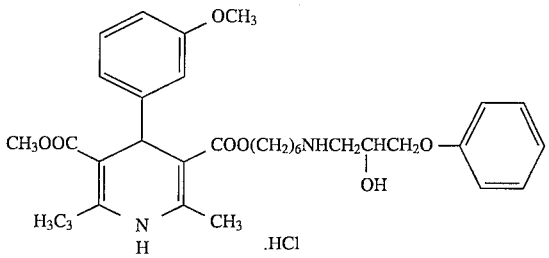

6-(2-hydroxy-3-phenoxypropylamino)hexyl methyl 2,6-dimethyl-4-(m-methoxyphenyl)-1,4-dihyrdopyridine-3,5-dicarboxylate hydrochloride (I) amorphous powder
(II) Anal ($C_{32}H_{42}N_2O_7 \cdot HCl \cdot H_2O$)

|  | C (%) | H (%) | N (%) | Cl (%) |
|---|---|---|---|---|
| Cal | 62.42 | 7.27 | 4.55 | 5.76 |
| Fnd | 62.43 | 7.33 | 4.53 | 5.92 |

(III) NMR (CDCl$_3$)
(free form)
δ: 2.28 (3H, s)
2.29 (3H, s)
3.64 (3H, s)
3.74 (3H, s)
5.00 (1H, s)
6.34 (1H, s)

Example 47

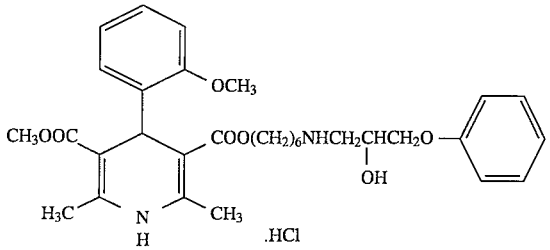

6-(2-hydroxy-3-phenoxypropylamino)hexyl methyl 2,6-dimethyl-4-(o-methoxyphenyl)-1,4-dihydropyridine-3,5-dicarboxylate hydrochloride (I) amorphous powder
(II) Anal ($C_{32}H_{42}N_2O_7 \cdot HCl$)

|  | C (%) | H (%) | N (%) |
|---|---|---|---|
| Cal | 63.72 | 7.19 | 4.64 |
| Fnd | 59.27 | 7.23 | 4.41 |

(III) NMR (CDCl$_3$)
(free form)
δ: 2.27 (3H, s)
2.29 (3H, s)
3.61 (3H, s)
3.78 (3H, s)
5.28 (1H, s)
5.62 (1H, s)

Example 48

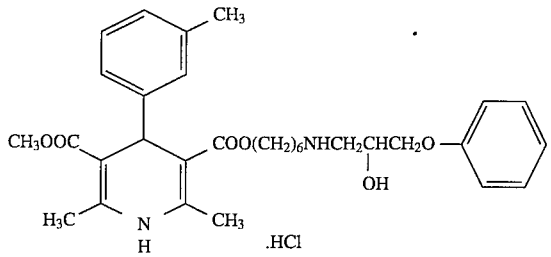

6-(2-hydroxy-3-phenoxypropylamino)hexyl methyl 2,6-dimethyl-4-(m-methylphenyl)-1,4-dihydro-pyridine-3,5-dicarboxylate hydrochloride
(I)     amorphous powder
(II)    Anal (C₃₂H₄₂N₂O₆·HCl·0.9 H₂O)

|  | C (%) | H (%) | N (%) | Cl (%) |
|---|---|---|---|---|
| Cal | 63.70 | 7.48 | 4.64 | 5.88 |
| Fnd | 63.82 | 7.73 | 4.66 | 5.78 |

(III)   NMR     (CDCl₃)
        (free form)
   δ:   2.28 (3H, s)
        2.32 (3H, s)
        2.33 (3H, s)
        3.64 (3H, s)
        4.97 (1H, s)
        5.69 (1H, s)

Example 49

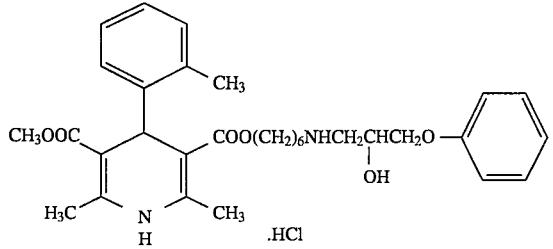

6-(2-hydroxy-3-phenoxypropylamino)hexyl methyl 2,6-dimethyl-4-(o-methylphenyl)-1,4-dihydro-pyridine-3,5-dicarboxylate hydrochloride
(I)     amorphous powder
(II)    Anal (C₃₂H₄₂N₂O₇·HCl)

|  | C (%) | H (%) | N (%) |
|---|---|---|---|
| Cal | 65.46 | 7.38 | 4.77 |
| Fnd | 62.83 | 7.57 | 4.82 |

(III)   NMR     (CDCl₃)
        (free form)
   δ:   2.29 (3H, s)
        2.30 (3H, s)
        2.54 (3H, s)
        3.61 (3H, s)
        5.15 (1H, s)
        5.67 (1H, s)

Example 50

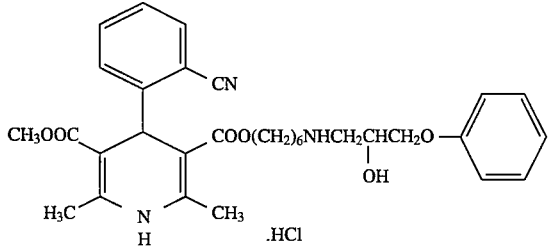

6-(2-hydroxy-3-phenoxypropylamino)hexyl methyl 4-(o-cyanophenyl)-2,6-dimethyl-1,4-dihydro-pyridine-3,5-dicarboxylate hydrochloride
(I)     amorphous powder
(II)    Anal (C₃₂H₃₉N₃O₄·HCl·H₂O)

|  | C (%) | H (%) | N (%) |
|---|---|---|---|
| Cal | 62.38 | 6.87 | 6.82 |
| Fnd | 62.23 | 6.81 | 6.66 |

(III)   NMR     (CDCl₃)
        (free form)
   δ:   2.32 (3H, s)
        2.35 (3H, s)
        3.65 (3H, s)
        5.30 (1H, s)
        6.06 (1H, s)

Example 51

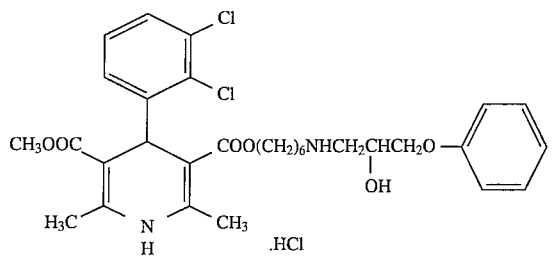

6-(2-hydroxy-3-phenoxypropylamino)hexyl methyl 4-(2,3-dichlorophenyl)-2,6-dimethyl-1,4-dihydro-pyridine-3,5-dicarboxylate hydrochloride
(I) amorphous powder
(II) Anal ($C_{31}H_{38}N_2O_6Cl_2 \cdot HCl \cdot 1.3\ H_2O$)

|  | C (%) | H (%) | N (%) |
|---|---|---|---|
| Cal | 55.95 | 6.30 | 4.21 |
| Fnd | 55.94 | 6.30 | 4.18 |

(III) NMR (CDCl$_3$)
(free form)
δ: 2.28 (3H, s)
2.31 (3H, s)
3.61 (3H, s)
5.45 (1H, s)
5.82 (1H, s)

Example 52

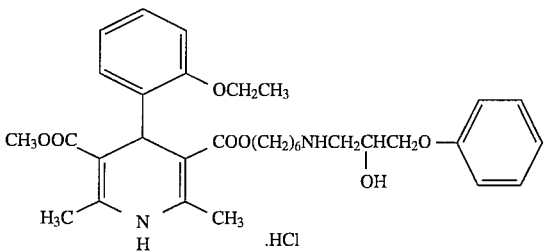

6-(2-hydroxy-3-phenoxypropylamino)hexyl methyl 2,6-dimethyl-4-(o-ethoxyphenyl)-1,4-dihydro-pyridine-3,5-dicarboxylate hydrochloride
(I) amorphous powder
(II) Anal ($C_{33}H_{44}N_2O_7 \cdot HCl \cdot H_2O$)

|  | C (%) | H (%) | N (%) |
|---|---|---|---|
| Cal | 62.40 | 7.46 | 4.41 |
| Fnd | 62.16 | 7.67 | 4.20 |

(III) NMR (CDCl$_3$)
(free form)
δ: 2.24 (3H, s)
2.28 (3H, s)
3.58 (3H, s)
5.22 (1H, s)
5.76 (1H, s)

Example 53

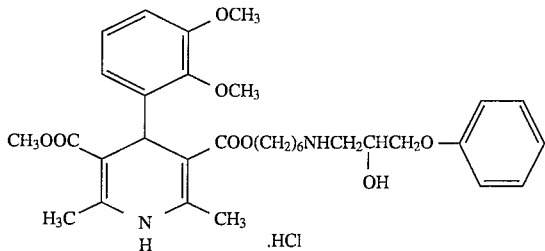

6-(2-hydroxy-3-phenoxypropylamino)hexyl 4-(2,3-dimethoxyphenyl)-2,6-dimethyl-1,4-dihydro-pyridine-3,5-dicarboxylate hydrochloride
(I) amorphous powder
(II) Anal ($C_{33}H_{44}N_2O_4 \cdot HCl \cdot H_2O$

|  | C (%) | H (%) | N (%) |
|---|---|---|---|
| Cal | 60.87 | 7.27 | 4.30 |
| Fnd | 61.05 | 7.52 | 4.19 |

(III) NMR (CDCl$_3$)

|   |   |
|---|---|
| | (free form) |
| δ: | 2.25 (3H, s) |
| | 2.27 (3H, s) |
| | 3.61 (3H, s) |
| | 3.78 (3H, s) |
| | 3.80 (3H, s) |
| | 5.20 (1H, s) |
| | 5.89 (1H, s) |

Example 54

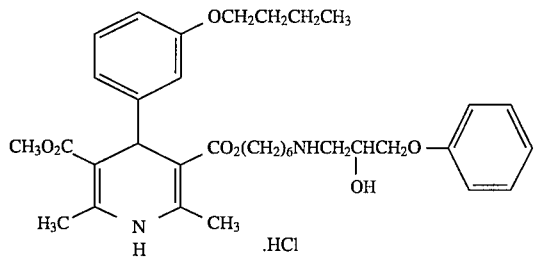

6-(2-hydroxy-3-phenoxypropylamino)hexyl methyl 2,6-dimethyl-4-(m-butoxyphenyl)-1,4-dihydro-pyridine-3,5-dicarboxylate hydrochloride
(I) amorphous powder
(II) Anal ($C_{35}H_{48}N_2O_7 \cdot HCl$)

|  | C (%) | H (%) | N (%) |
|---|---|---|---|
| Cal | 65.15 | 7.65 | 4.34 |
| Fnd | 65.22 | 7.80 | 4.51 |

(III) NMR (CDCl$_3$)
(free form)
δ: 0.96 (3H, t)
2.32 (6H, s)
3.64 (3H, s)
5.72 (1H, s)

Example 55

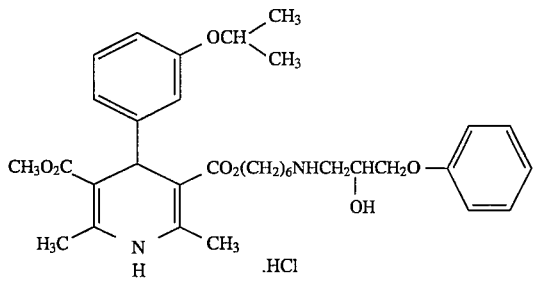

6-(2-hydroxy-3-phenoxypropylamino)hexyl methyl 2,6-dimethyl-4-(m-isopropoxyphenyl)-1,4-dihydropyridine-3,5-dicarboxylate hydrochloride
(I) amorphous powder
(II) Anal ($C_{34}H_{46}N_2O_7 \cdot HCl$)

|  | C (%) | H (%) | N (%) |
|---|---|---|---|
| Cal | 64.70 | 7.50 | 4.44 |
| Fnd | 64.58 | 7.70 | 4.68 |

(III) NMR (CDCl$_3$)
(free form)
δ: 1.30 (6H, d)
2.30 (3H, s)
2.32 (3H, s)
3.64 (3H, s)
4.96 (1H, s)

Example 56

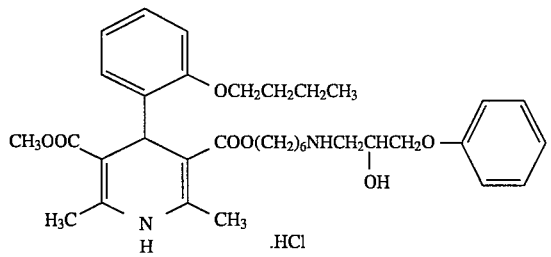

6-(2-hydroxy-3-phenoxypropylamino)hexyl methyl 4-(o-butoxyphenyl)-2,6-dimethyl-1,4-dihydro-
pyridine-3,5-dicarboxylate hydrochloride
(I) amorphous powder
(II) Anal ($C_{35}H_{49}N_2O_7Cl$)

|  | C (%) | H (%) | N (%) |
|---|---|---|---|
| Cal | 65.15 | 7.65 | 4.34 |
| Fnd | 63.94 | 7.70 | 4.38 |

(III) NMR (CDCl$_3$)
(free form)
δ: 0.96 (3H, t)
2.22 (3H, s)
2.24 (3H, s)
2.64 (2H, t)
3.56 (3H, s)
5.22 (1H, s)

Example 57

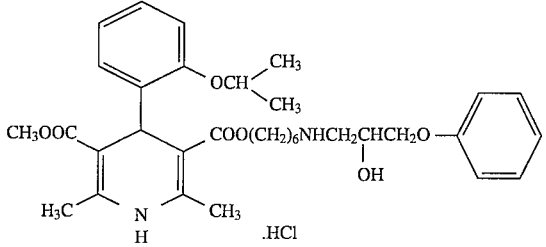

6-(2-hydroxy-3-phenoxypropylamino)hexyl methyl 4-(o-isopropoxyphenyl)-2,6-dimethyl-1,4-dihydro-
pyridine-3,5-dicarboxylate hydrochloride
(I) amorphous powder
(II) Anal ($C_{33}H_{47}N_2O_7Cl$)

|  | C (%) | H (%) | N (%) |
|---|---|---|---|
| Cal | 64.70 | 7.51 | 4.44 |
| Fnd | 64.90 | 7.29 | 4.27 |

(III) NMR (CDCl$_3$)
(free form)
δ: 1.24 (6H, d)
2.20 (3H, s)
2.24 (3H, s)
3.56 (3H, s)
4.32 (1H, m)
5.10 (1H, s)

Example 58

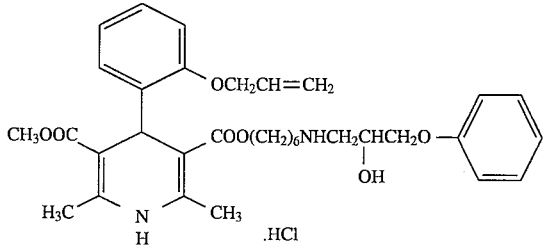

6-(2-hydroxy-3-phenoxypropylamino)hexyl methyl 4-(o-allyloxyphenyl)-2,6-dimethyl-1,4-dihydro-
pyridine-3,5-dicarboxylate hydrochloride
(I) amorphous powder
(II) Anal ($C_{34}H_{45}N_2O_7Cl$)

|  | C (%) | H (%) | N (%) |
|---|---|---|---|
| Cal | 64.90 | 7.21 | 4.45 |
| Fnd | 64.59 | 7.14 | 4.20 |

(III) NMR (CDCl$_3$)
(free form)
δ: 2.22 (3H, s)
2.26 (3H, s)
2.64 (2H, t)
3.56 (3H, s)
5.28 (1H, s)
5.70–6.40 (1H, m)

We claim:
1. A pharmaceutical composition possessing both calcium (2+)-antagonistic and beta-receptor blocking activities which contains as the active ingredient thereof, 4-(2-hydroxy-3-phenoxypropylamino)butyl methyl 2,6-dimethyl-4-(m-nitrophenyl)-1,4-dihydropyridine-3,5 dicarboxylate.

* * * * *